(12) United States Patent
Barton et al.

(10) Patent No.: US 8,501,162 B2
(45) Date of Patent: Aug. 6, 2013

(54) COMPOSITIONS AND METHODS FOR THE SKIN AND HAIR

(75) Inventors: Stephen Peter Barton, Nottingham (GB); Mark Johnson, Nottingham (GB); Paul James Tomlinson, Nottingham (GB)

(73) Assignee: The Boots Company PLC, Nottingham, Nottinghamshire (GB)

( * ) Notice: Subject to any disclaimer, the term of this patent is extended or adjusted under 35 U.S.C. 154(b) by 0 days.

(21) Appl. No.: 12/681,410

(22) PCT Filed: Sep. 29, 2008

(86) PCT No.: PCT/GB2008/050878
§ 371 (c)(1),
(2), (4) Date: Apr. 2, 2010

(87) PCT Pub. No.: WO2009/044190
PCT Pub. Date: Apr. 9, 2009

(65) Prior Publication Data
US 2010/0221202 A1    Sep. 2, 2010

(30) Foreign Application Priority Data
Oct. 2, 2007 (GB) .................................. 0719202.4

(51) Int. Cl.
*A61K 8/97* (2006.01)
*A61K 36/53* (2006.01)
*A61K 36/16* (2006.01)
*A61Q 17/04* (2006.01)
*A61Q 5/00* (2006.01)

(52) U.S. Cl.
USPC ............ 424/59; 424/70.9; 424/725; 424/752; 424/770; 424/775

(58) Field of Classification Search
None
See application file for complete search history.

(56) References Cited

U.S. PATENT DOCUMENTS

| | | | |
|---|---|---|---|
| 5,470,874 A * | 11/1995 | Lerner | |
| 5,552,158 A * | 9/1996 | Evans et al. | |
| 6,362,167 B1 * | 3/2002 | Ghosal | |
| 2003/0008048 A1 | 1/2003 | Winston et al. | |
| 2003/0165444 A1 | 9/2003 | Cals-Grierson | |
| 2005/0036963 A1 * | 2/2005 | Sah et al. | |
| 2006/0182708 A1 | 8/2006 | Bockmuhl et al. | |
| 2007/0003536 A1 | 1/2007 | Zimmerman et al. | |

FOREIGN PATENT DOCUMENTS

| | | | |
|---|---|---|---|
| DE | 10259014 A1 * | 6/2004 | |
| DE | 20204402807 U1 * | 11/2004 | |
| JP | 03227985 A * | 10/1991 | |
| WO | WO 9414414 A1 * | 7/1994 | |

OTHER PUBLICATIONS

Hibatallah J, Carduner C, Poelman MC. J Pharm Pharmacol. Dec. 1999;51(12):1435-40. In-vivo and in-vitro assessment of the free-radical-scavenger activity of Ginkgo flavone glycosides at high concentration.).*

Wikepdia: "Romarin"; Downloaded from world-wide-web Aug. 29, 2011.*

Messeguer et al. Int J Cosmet Sci. Oct. 2005;27(5):271-8. New anti-RNS and -RCS products for cosmetic treatment.*

* cited by examiner

*Primary Examiner* — Michele Flood
(74) *Attorney, Agent, or Firm* — Rothwell, Figg, Ernst & Manbeck, P.C.

(57) ABSTRACT

A composition for the prevention or inhibition of free radical-induced effect on the skin and/or hair comprises at least three antioxidant agents selected from the group consisting of ginkgo extract, emblica extract, dimethylmethoxy chromanol, pine bark extract, and rosemary extract.

19 Claims, 20 Drawing Sheets

Figure 1
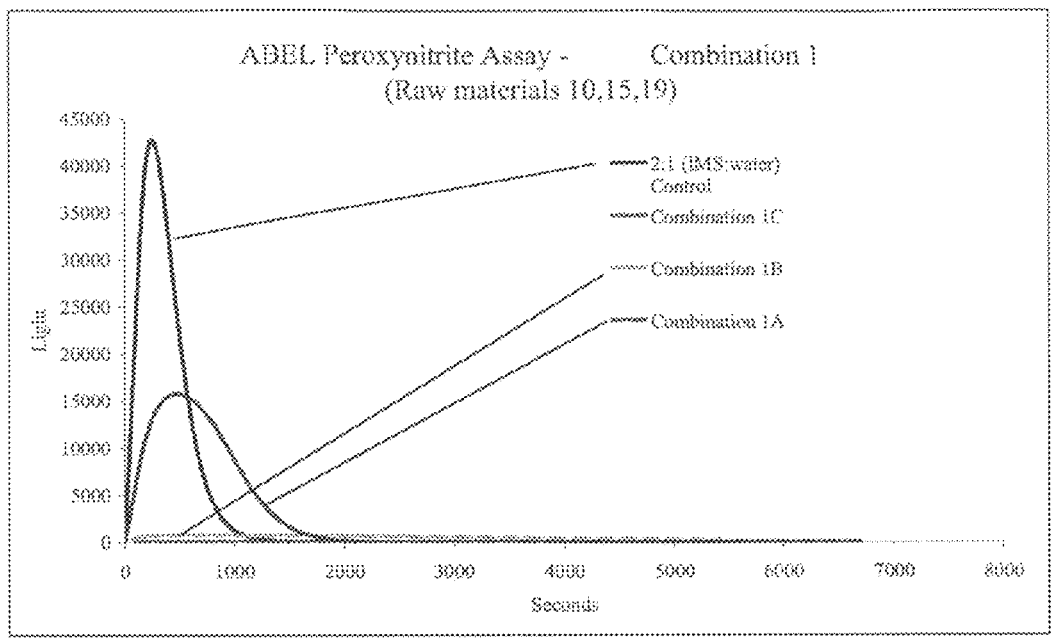
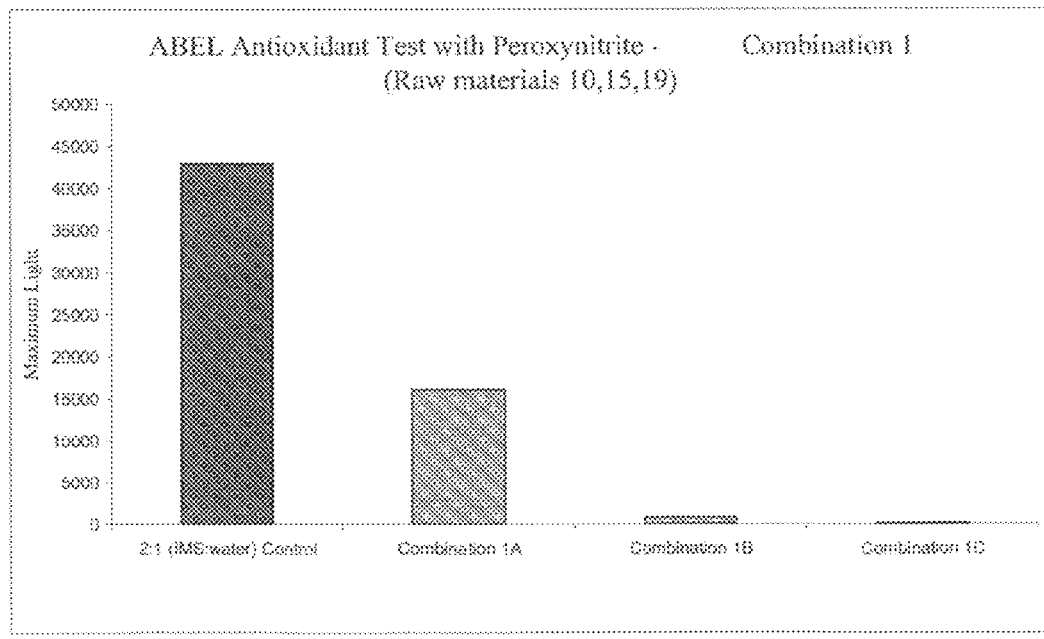

Figure 11
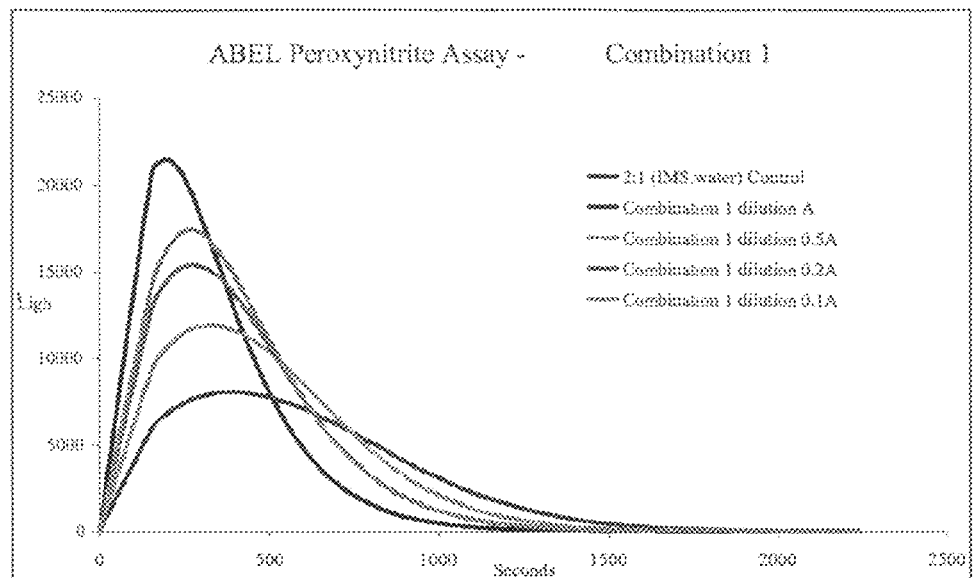
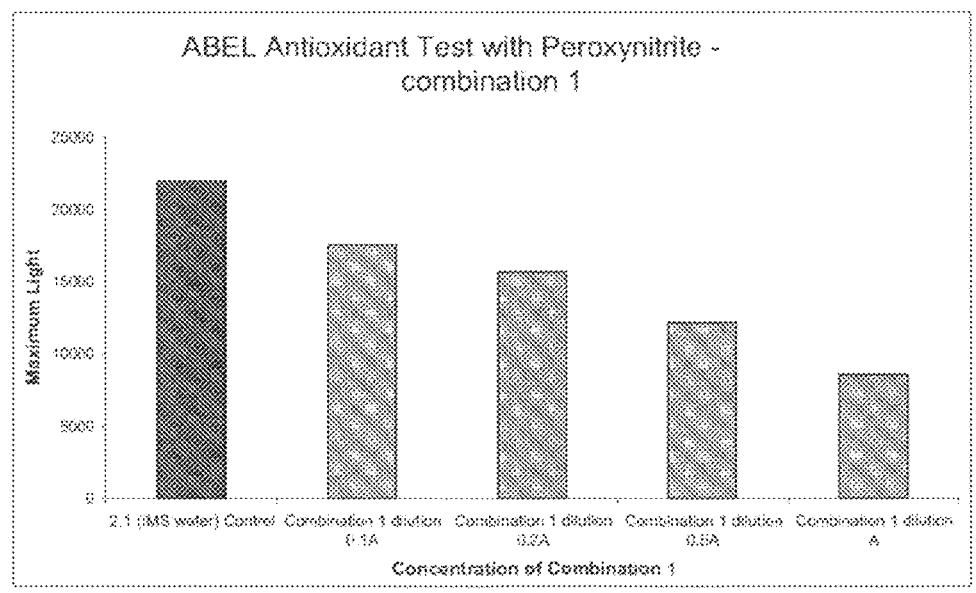

Figure 12
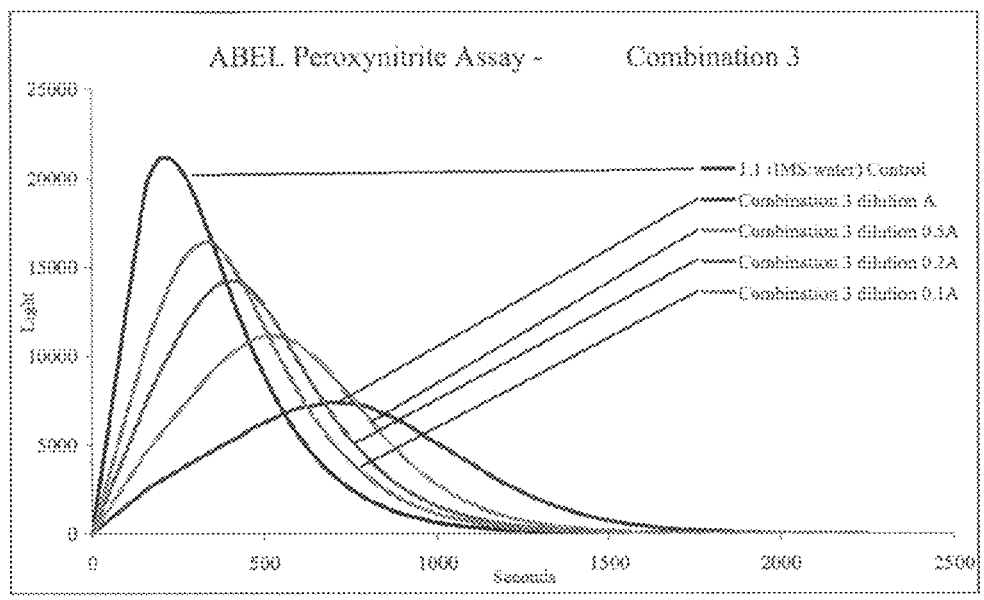
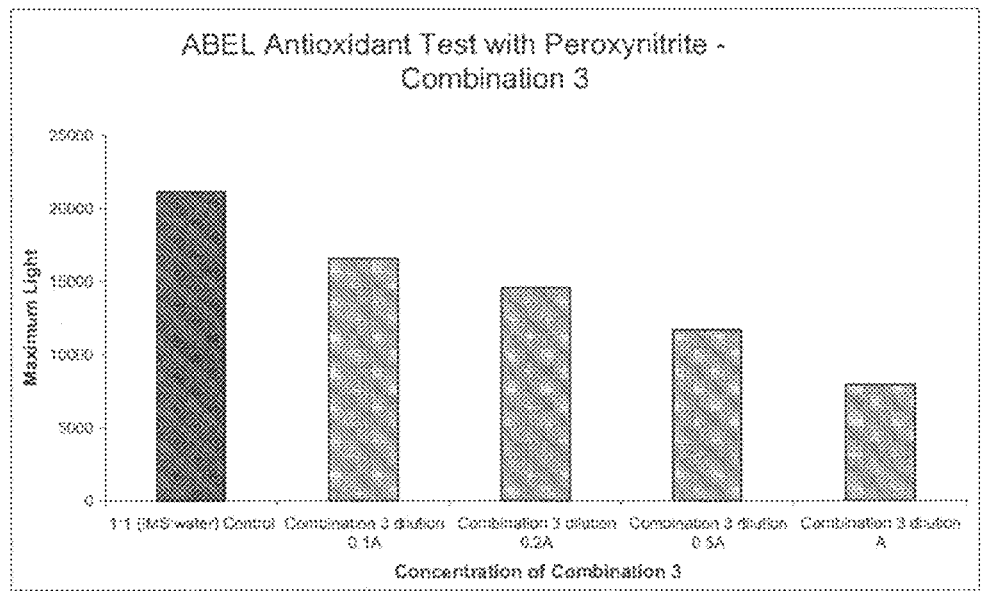

Figure 13
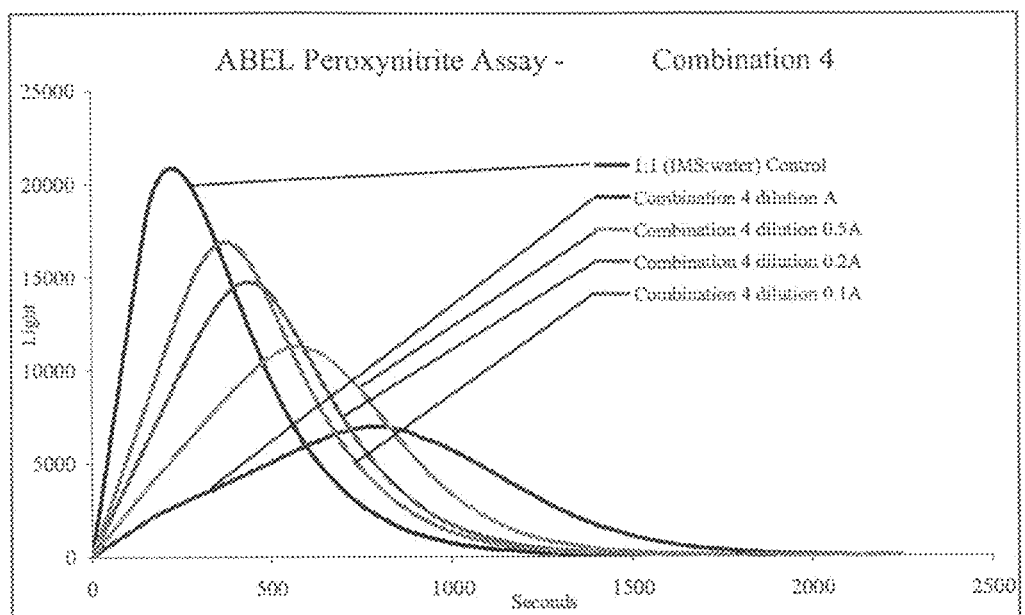
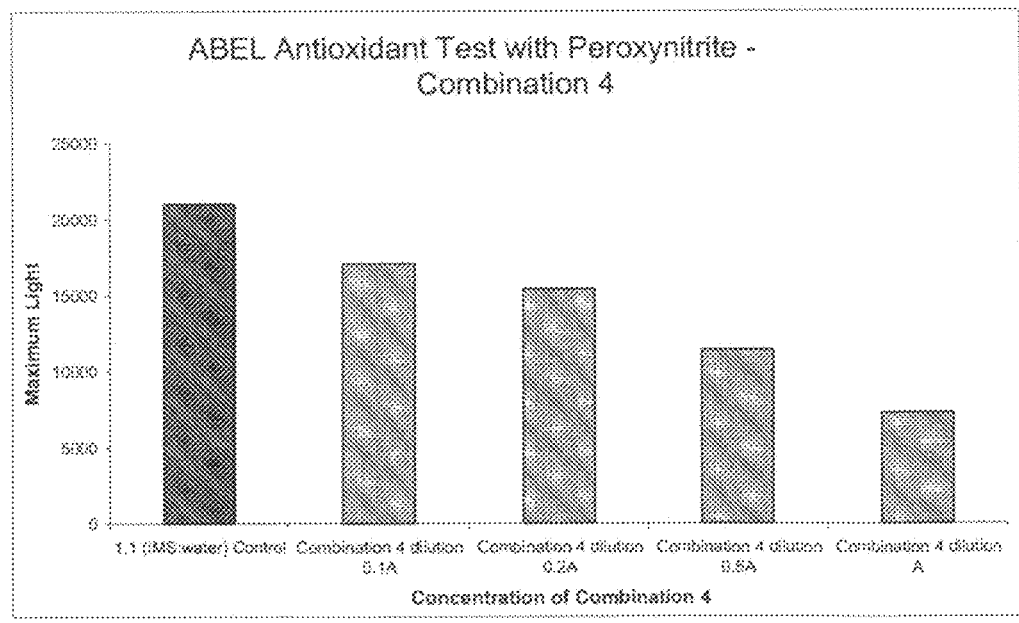

Figure 14
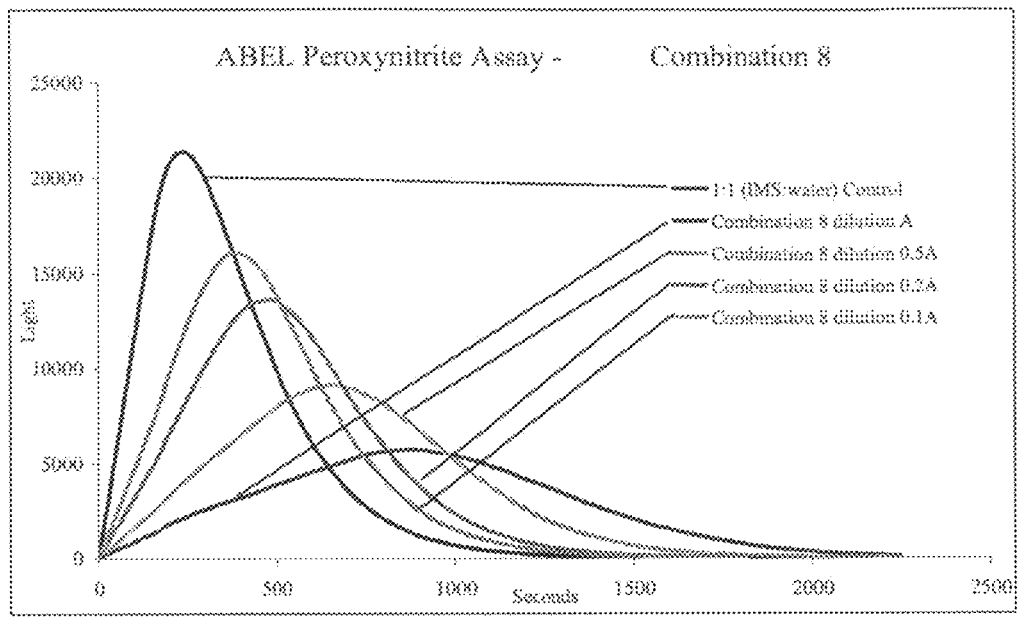
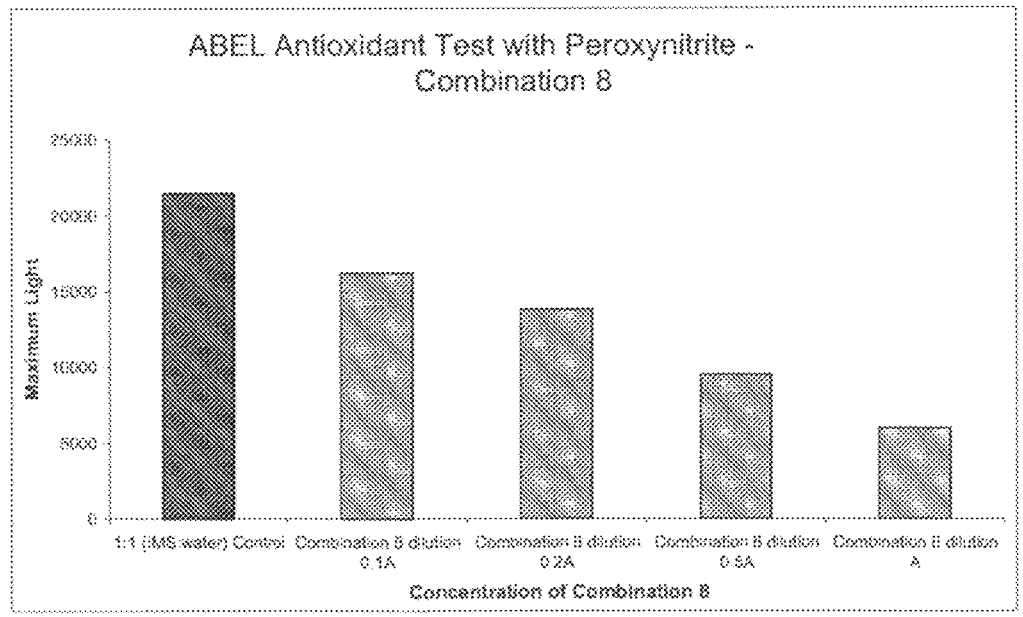

Figure 18
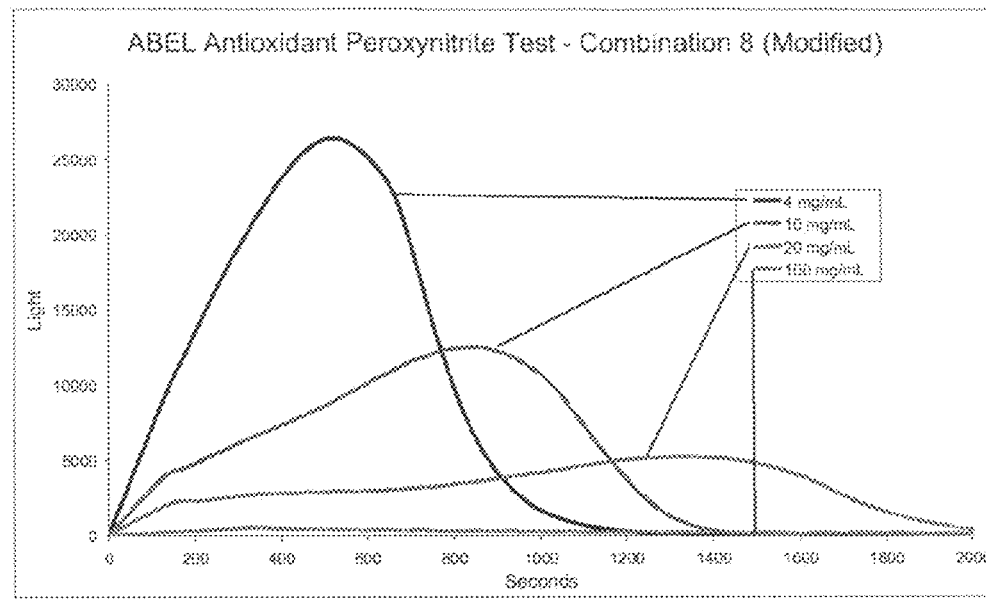
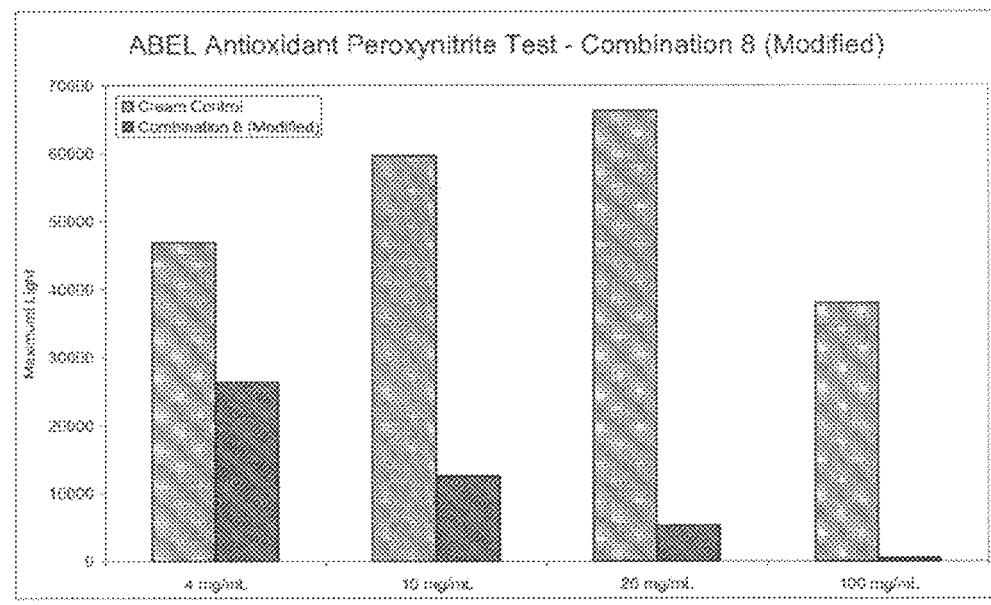

Figure 20
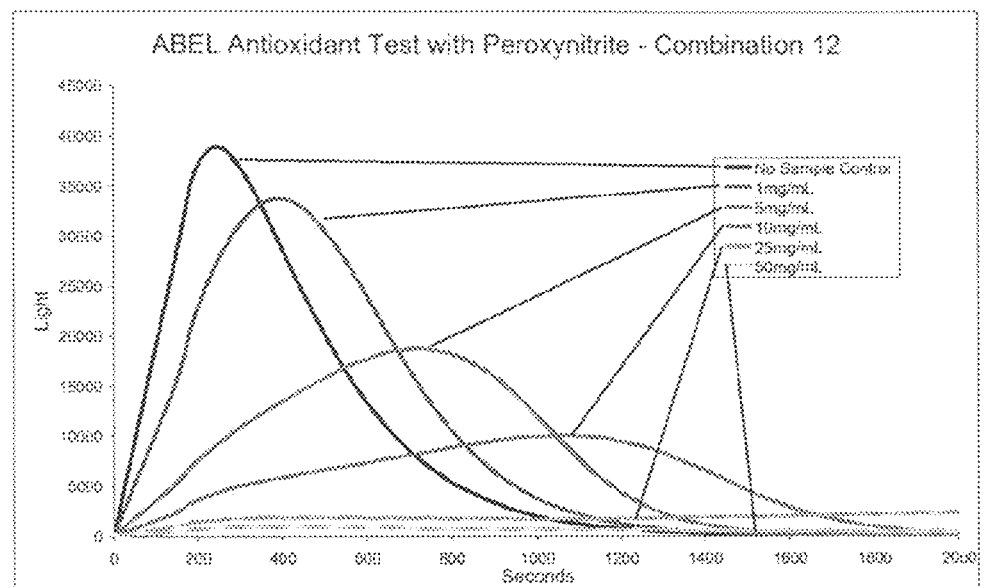
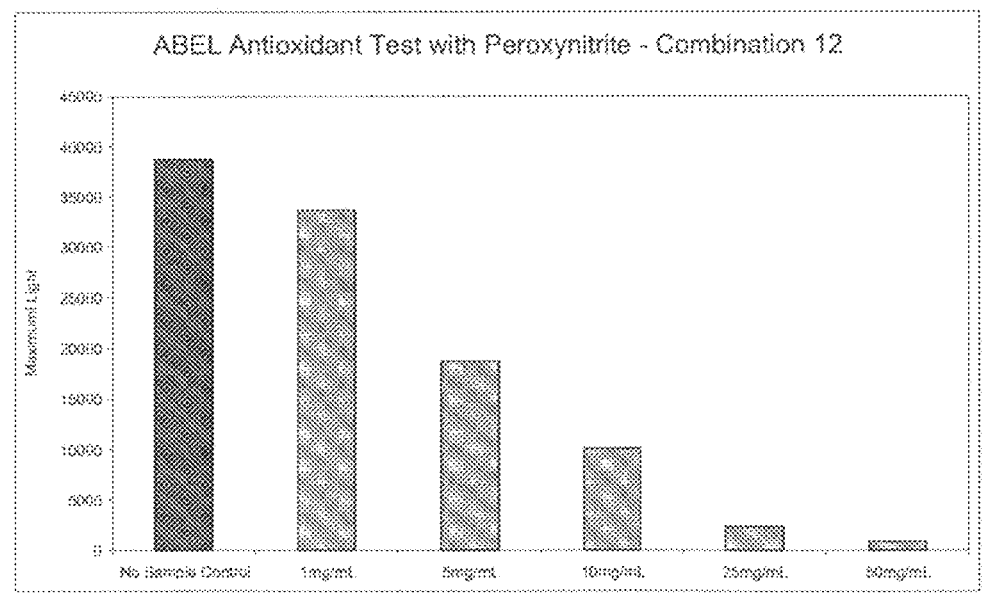

COMPOSITIONS AND METHODS FOR THE SKIN AND HAIR

CROSS REFERENCE TO RELATED APPLICATION

This application is a 35 U.S.C. 371 National Phase Entry Application from PCT/GB2008/050878, filed Sep. 29, 2008, which claims the benefit of Great Britain Patent Application No. 0719202.4 filed on Oct. 2, 2007, the disclosure of which is incorporated herein in its entirety by reference.

FIELD OF THE INVENTION

This invention relates to compositions providing enhanced protection for the skin and hair against the adverse effects of free radicals, eg effects mediated by UV-radiation, or other sources of oxidative stress. In particular aspects, the invention provides topical compositions containing combinations of antioxidant agents effective in protecting the skin and/or hair against damage due to free radicals, and compositions intended for oral administration that provide systemic protection against such damage.

BACKGROUND OF THE INVENTION

As we age, our skin undergoes changes such as becoming thinner, more easily damaged and less elastic. In addition, lifetime exposure to UV-A and UV-B radiation, together with other environmental factors that induce the formation of free radicals, such as pollution from traffic fumes, ozone, cigarette smoke etc, causes changes to the skin. These changes, including lines and wrinkling, actinic lentigines, dyspigmentation, rough skin, actinic telangiectasia and further loss of skin elastic function are due to direct UV-mediated damage to cells and indirectly mediated damage caused by the generation of free radicals in cells and tissues. This is generally termed photoageing and can account for up to 90% of the skin changes we associate with ageing.

The deleterious effects of UV radiation are generally believed to be due to the creation of free radicals. These highly reactive species may react with and damage DNA molecules in the skin (or elsewhere). Similar effects can also be attributed to radiation in the visible part of the spectrum.

Our hair also is damaged by exposure to UV-A and UV-B radiation, and other environmental factors that induce the formation of free radicals, such as those mentioned above. Furthermore, exposure to heat during drying and/or styling, and chemical treatment of the hair (eg perming, straightening, dyeing and/or bleaching) can also generate free radicals. Free radicals are implicated in the process of damage to hair, which may be observed as a reduction in shine, feel and/or fading of hair colour.

It is known to use antioxidant compounds as free radical quenchers, thereby mitigating the effects of free radical formation.

There have now been devised compositions and methods involving combinations of antioxidant agents which have been found to be particularly effective in protecting the skin and hair against free radical-induced damage.

BRIEF SUMMARY OF THE INVENTION

The invention utilises combinations of antioxidant agents including at least three antioxidants selected from the following list (list A):
ginkgo extract
emblica extract
dimethylmethoxy chromanol
pine bark extract
rosemary extract In a first aspect, the invention provides a composition for the prevention or inhibition of free radical-induced effect on the skin and/or hair, which composition comprises at least three antioxidant agents selected from List A.

In another aspect, the invention provides a method for the prevention or inhibition of free radical-induced effects on the skin and/or hair, which method comprises the administration to the hair and/or skin of a composition comprising at least three antioxidant agents selected from List A.

The invention further comprises the use of at least three antioxidant agents selected from List A in the manufacture of a composition for the prevention or inhibition of free radical-induced effects on the skin and/or hair.

The methods and compositions of the present invention are advantageous primarily in that they may protect the skin and/or hair more effectively from the effects of UV-induced free radical formation than known compositions. Therefore, the compositions and methods of the invention may be used to provide improved protection against damage to skin and/or hair caused by exposure to factors such as sunlight, environmental and/or atmospheric pollution. The improved protection may be due to achievement of a greater degree of protection, a greater duration of protection and/or a more rapid onset of protection. The method of the invention may have therapeutic benefits, but its primary effect may be cosmetic in that it improves or prevents degradation of the appearance of the skin and/or hair, eg due to the effects of exposure to external factors of the type that have been mentioned above, or in respect of the appearance of the skin due to ageing.

Some or all of the antioxidant agents used in the present invention may already be known to be effective as free radical quenchers and to prevent oxidative damage to the skin and/or hair. However, the present invention discloses that combinations of these agents may have a greater efficacy than that expected, ie the efficacy of the combination is greater that the sum of the individual agents. The combinations of antioxidant agents described by the present invention are therefore "synergistic". This has been demonstrated by in vitro testing.

Antioxidant agents are often either highly coloured or else they are variable in colour or change colour over time. If highly coloured antioxidant agents are used in amounts necessary to be totally effective, it is likely that the agents would give the composition a cosmetically unacceptable appearance. It is similarly undesirable for cosmetic products to vary in colour or to change colour over time, which may falsely suggest to the consumer that the product is chemically deteriorating or is sub-standard in quality. Moreover, the use of antioxidant agents can be costly. For those reasons, inter alia, many conventional skincare and haircare compositions use less antioxidant agent(s) than necessary to provide total protection. Indeed, it may be the case that the base composition itself has a pro-oxidant effect, and therefore an increased concentration of antioxidant agent(s) is required to achieve the desired level of protection. With the present invention, because of the increased efficacy of the synergistic mixture of antioxidant agents, it is possible to include the antioxidant agents in sufficient amounts to provide an effective defense against the action of free radicals. Alternatively, if the same level of protection as a conventional formulation is required, then the increased efficacy of the synergistic mixture of antioxidant agents means that the composition will require lower quantities of the antioxidant agents than a conventional formulation. Hence, problems with highly coloured formulations may be reduced (cosmetic appearance), and the cost of the formulation is likely to be lower as well.

The combinations of antioxidant agents according to the invention may be administered by a variety of routes. The antioxidants have been found to be particularly suitable for inclusion in compositions for topical administration to the skin and/or hair. However, the combinations of antioxidants are also suitable for systemic administration, in particular oral administration.

Thus, according to a further aspect of the invention there is provided a composition for the prevention or inhibition of free radical-induced effects on the skin and/or hair, which composition is in a form suitable for oral administration and comprises at least three antioxidant agents selected from List A.

In another aspect, the invention provides a method for the prevention or inhibition of free radical-induced effects on the skin and/or hair, which method comprises the oral administration of a composition comprising at least three antioxidant agents selected from List A.

The invention further comprises the use of at least three antioxidant agents selected from List A, in the manufacture of a composition for the prevention or inhibition of free radical-induced effects on the skin and/or hair, the composition being in a form suitable for oral administration.

It is generally preferred that the antioxidant agents selected from List A include at least one water-soluble antioxidant and at least one oil-soluble antioxidant. By water-soluble is meant that the antioxidant should be preferentially soluble in the water phase (ie aqueous phase) of a water-in-oil or an oil-in-water system. Similarly, by oil-soluble is meant that the antioxidant should preferentially be soluble in the oil phase of a water-in-oil or an oil-in-water system. By preferably soluble is meant that more than 50% by weight of the antioxidant dissolves in the respective water or oil phase. The water-soluble antioxidants may be such that more than 60%, more than 70%, more than 80%, or more than 90% by weight of the antioxidant dissolves in the water phase or the oil phase, respectively.

In certain embodiments, the compositions of the invention comprise dimethylmethoxy chromanol in combination with at least two further antioxidants selected from List A.

In combination, the amount of the at least three antioxidant agents selected from List A may range from 0.0001% to 10% by weight of the total composition, preferably from 0.001% to 1% by weight of the total composition and most preferably from 0.001% to 0.1% by weight of the total composition.

Preferred compositions comprise ginkgo extract, emblica extract and a further antioxidant agent selected from List A, preferably dimethylmethoxy chromanol or rosemary extract, most preferably dimethylmethoxy chromanol.

Preferred compositions comprise emblica extract, dimethylmethoxy chromanol and a further antioxidant agent selected from List A, most preferably ginkgo extract.

Preferred compositions comprise emblica extract, rosemary extract and a further antioxidant agent selected from List A, preferably ginkgo extract or dimethylmethoxy chromanol.

Preferred compositions comprise dimethylmethoxy chromanol, pine bark extract and a further antioxidant agent selected from List A, preferably emblica extract or rosemary extract, most preferably rosemary extract.

Preferred compositions comprise dimethylmethoxy chromanol, rosemary extract and a further antioxidant agent selected from List A, preferably emblica extract or pine bark extract, most preferably pine bark extract.

In one embodiment, compositions comprise dimethylmethoxy chromanol, pine bark extract and rosemary extract. Preferably the ratio by weight of dimethylmethoxy chromanol:pine bark extract:rosemary extract in the composition is D:P:R, where D is 15 to 25, P is 15 to 25 and R is 10. In certain embodiments, the ratio D:P:R is about 18:about 17:10.

In another embodiment, compositions comprise emblica extract, dimethylmethoxy chromanol and rosemary extract. Preferably the ratio by weight of emblica extract:dimethylmethoxy chromanol:rosemary extract in the composition is E:D:R, where E is 10 to 20, D is 15 to 25 and R is 1. In certain embodiments, the ratio E:D:R is about 13:about 18:1.

In another embodiment, compositions comprise emblica extract, dimethylmethoxy chromanol and pine bark extract. Preferably the ratio by weight of emblica extract:dimethylmethoxy chromanol:pine bark extract in the composition is E:D:P, where E is 10 to 20, D is 0.5 to 3 and P is 0.5 to 3. In certain embodiments, the ratio of E:D:P is about 13:about 1.8:about 1.7.

In another embodiment, compositions comprise ginkgo extract, emblica extract and dimethylmethoxy chromanol. Preferably, the ratio by weight of ginkgo extract:emblica extract:dimethylmethoxy chromanol in the composition is G:E:D, where G is 1, E is 0.5 to 10, and D is 0.05 to 15. In certain embodiments G:E:D is about 18:about 13:about 1.8; about 1.8:about 13:about 18; about 20:about 15:about 20; about 5:about 15:about 20; or about 10:about 15:about 20. Most preferably the ratio is about 10:about 15:about 20.

In a further embodiment, compositions comprise ginkgo extract, emblica extract and rosemary extract. Preferably the ratio by weight of ginkgo extract:emblica extract:rosemary extract in the composition is G:E:R, where G is 15 to 25, E is 10 to 20 and R is 1. In certain embodiments, the ratio is about 18:about 13:1.

The antioxidants used in the invention are commercially available from numerous sources.

The ginkgo extract that is preferred for use in the invention is an extract of the leaf of *Ginkgo biloba*, for example Herbalia® Ginkgo obtained from Cognis Cognis Iberia S.L., Pg. Industrial San Vicente s/n, 08755 Castellbisbal, Barcelona, Spain. This product consists of 98% *Ginkgo biloba* leaf extract and 2% silica. It may be processed for use in the invention by making a solution in glycerin prior to its addition to the bulk composition at a temperature below 35° C. The amount of glycerin used to dissolve the ginkgo extract may be, for example, about 2% by weight of the total composition.

The emblica extract preferred for use in the invention is a 100% *Phyllanthus emblica* fruit extract sold under the trade name Emblica™ by Merck Speciality Chemicals Merck KgaA, Dept. Pigments/Cosmetics, 64271 Darmstadt, Germany. It is understood that the major ingredients are emblicanin-A, emblicanin-B, pedunculagin, punigluconin, rutin and gallic acid; emblicanin-A, emblicanin-B and emblicanin-oligomers being the key active ingredients. About 90% of this extract is water-soluble and about 10% is oil-soluble. It may be processed for use in the invention by making a solution in water prior to addition to the bulk composition at a temperature below 35° C. The amount of water used to dissolve the emblica extract may be, for example, about 2% by weight of the total composition.

Dimethylmethoxy chromanol is a synthetic analogue of gamma tocopherol (vitamin E). Other chemical names include 2H-1-benzopyran-6-ol and 3,4-dihydro-7-methoxy-2,2-dimethyl. It may be obtained from Lipotec S.A Poligon Industrial Camri Ral, C/Isaac Peral, 17 08850 Gava, Barcelona, Spain, under the trade name Lipochroman-6. It is oil soluble, and may be processed for use in the invention by making a solution in ethanol prior to addition to the bulk composition at a temperature below 35° C. The amount of ethanol used to dissolve the dimethylmethoxy chromanol may be, for example, about 0.5% by weight of the total composition.

Pine (*Pinus pinaster*) bark extract is a natural extract from the bark of the maritime pine tree, and may be obtained commercially under the trade name Oligopin from DRT, 30 Rue Gambetta, B. P. 206, 40105 DAX Cedex, France. Pine bark extract may also be obtained commercially under the trade name Pycnogenol®. It is partially oil soluble and partially water soluble, and may be processed for use in the invention by dissolving in 1:1 water:ethanol prior to addition to the bulk composition at a temperature below 35° C.

Rosemary extract refers to extract of *Rosmarinus officinalis*. It is commercially available, for example, as the Rosemary extract RA supplied by Vitiva, Nova vas 98, 2281 Markovci, Slovenia. It may be processed for use in the invention by dissolving in 1:1 water:ethanol prior to addition to the bulk composition at a temperature below 35° C.

Preferred compositions may further comprise ascorbic acid, or a salt, ester, glucoside, glucosamine and/or other derivative thereof. The ascorbic acid component may comprise ascorbic acid itself, but more preferably comprises a derivative of ascorbic acid. Examples of such derivatives include salts, eg sodium and calcium ascorbate, or esters with inorganic and organic acids, eg ascorbyl phosphate and ascorbyl palmitate, or esters with glucose derivatives, eg ascorbyl glucoside. The ascorbic acid component of the composition may be the ascorbic acid-derived product sold as "Ester-C" by Inter-Cal Nutraceuticals of Prescott, Ariz., USA. That product is understood to include calcium ascorbate, together with one or more derivatives of aldonic acids, particularly threonic acid; that are metabolites of ascorbic acid. Most preferably, the ascorbic acid component of the composition is the ascorbyl glucoside sold as "AA2G" (Ascorbic Acid 2-Glucoside) by Hayashibara.

The amount of ascorbic acid component in the composition may range from 0.0001% to 10% by weight of the total composition, preferably from 0.001% to 1% by weight of the total composition and most preferably from 0.01% to 0.1% by weight of the total composition.

Compositions according to the invention may include additional active ingredients.

Particularly preferred additional actives include one or more agents selected from the following list (List B):
white lupin peptides
palmitoyl oligopeptide and palmitoyl tetrapeptides
retinyl palmitate.

Preferred compositions according to the invention comprise the following combination of agents from List A and List B:

Dimethylmethoxy chromanol, pine bark extract, rosemary extract, white lupin peptides, palmitoyl oligopeptide and palmitoyl tetrapeptides, and retinyl palmitate.

Emblica extract, dimethylmethoxy chromanol, rosemary extract, white lupin peptides, palmitoyl oligopeptide and palmitoyl tetrapeptides, and retinyl palmitate.

Emblica extract, dimethylmethoxy chromanol, pine bark extract, white lupin peptides, palmitoyl oligopeptide and palmitoyl tetrapeptides, and retinyl palmitate.

Ginkgo extract, emblica extract, dimethylmethoxy chromanol, white lupin 20, peptides, palmitoyl oligopeptide and palmitoyl tetrapeptides, and retinyl palmitate.

Ginkgo extract, emblica extract, rosemary extract, white lupin peptides, palmitoyl oligopeptide and palmitoyl tetrapeptides, and retinyl palmitate.

Most preferably, the above combinations additionally comprise ascorbic acid, or a salt, ester, glucoside, glucosamine and/or other derivative thereof.

The additional actives in List B are commercially available from numerous sources.

White lupin peptides refers to a hydrolysed peptide extract of sweet white lupin (*lupinus albus*) commercially available, for example, from Silab, BP 213-19108 Brive Cedex, France.

Palmitoyl oligopeptide and palmitoyl tetrapeptides may be obtained commercially as a single ingredient from Sederma, 29 Rue Du Chemin Vert BP 33, Le Perray En Yvelines, 78610 France, under the trade name Matrixyl™ 3000.

Retinyl palmitate, or Vitamin A palmitate, may be obtained commercially, for example, from DSM Nutritional Products, Postfach, CH-4070 Basel, Switzerland.

Additional active ingredients may include one or more further antioxidant ingredients. Preferred examples include:
ginseng extract (*Panax ginseng*);
mulberry concentrate (*Morus alba*);
rose hip extract (*Rosa canine*);
Japanese pagoda tree extract (*Sophora japonica*);
lutein;
Edelweiss extract (*Leontopodium alpinum*) available commercially for example under the trade name Alpaflor Edelweiss GC (900-01) from Alpaflor;
rice bran oil (*Oryza sativa*);
cranberry seed extract/oil (*Vaccinium macrocarpon*) commercially available for example under the trade name Cranberol™ from Chesham Chemicals Ltd;
alpha lipoic acid;
colourless carotenoids commercially available for example under the trade name IBR-CIC from Israeli Biotechnology Research;
Biodynes® $O_3$ (water and *saccaromyces* ferment filtrate lysate) commercially available from Arch Personal Care Products;
Einkorn extract (*Triticum monococcum*) available commercially for example under the trade name Phytoquintescine® from Vincience;
rooibus tea extract (*Aspalathus linearis*) available commercially for example as under the trade name Rooibus Herbasol from Cosmetochem Int Ltd;
Sweet Gale oil (*Myrica gale*);
Castaline®, in particular Castaline® LS9763 commercially available from Cognis;
astaxanthin commercially available for example as Aastapure® Natural Astaxanthin from Alga Technologies.

In certain embodiments, the compositions according to the invention comprise the antioxidant agents selected from List A, optionally in combination with ascorbic acid or a derivative thereof, as described above, but are free or substantially free of other antioxidant agents. By "substantially free" in this context is meant that the composition contains less than 5%, or less than 2%, or less than 1%, or less than 0.1% w/w of other antioxidant agents.

Compositions prepared in accordance with the invention may be formulated in any one of numerous different forms. Suitable types of composition, and methods by which they may be prepared, will generally be evident to those skilled in the art.

Topical Administration to the Skin

The present invention can be delivered to the skin via any of the conventional formulations known to those skilled in the art. The formulations may be "skincare" or "personal care" compositions, for example compositions marketed as moisturisers, cleansers, toners, masks or scrubs etc, for the face or body.

Equally, the compositions may be "cosmetic" compositions, which provide skincare benefits in addition to their principal cosmetic effect. Cosmetic formulations may be marketed, for example, as foundations, powders, lipsticks, eyeliners, eyeshadows, blushers, concealers, mascaras etc.

Typical formulation types are creams, lotions, gels, serums and powders.

One preferred group of compositions for application to the skin are formulated as emulsions. The emulsions may be o/w, w/o, o/w/o or w/o/w emulsions, which may be described inter alia as creams or lotions. Preferred emulsion compositions are o/w emulsions.

One preferred group of compositions for application to the skin are formulated as gels using a suitable thickener or gelling agent such as acrylates/C10-30 alkyl acrylate crosspolymer. Gel compositions may contain alcohol.

The composition will generally comprise other ingredients or excipients which constitute or form part of the dermatologically acceptable diluent or carrier and will be well known to those skilled in the art. These include, for example:

a) Humectants, eg glycerin, propylene glycol, butylene glycol, hexylene glycol, dipropylene glycol, polyethylene glycol, sorbitol, urea, xylitol, lactitol, lactic acid and salts, fructose, glucose, mannose, xylose, honey, pyrrolidone, and carboxylic acid and salts.

b) Emollients, eg PPG-15 stearyl ether, ethylhexyl stearate, cetyl dimethicone, octyldodecanol, PPG-20 methyl glucose ether, isopropyl myristate isopropyl palmitate, isopropyl laurate isodecyl laurate, isodecyl neopentanoate, isohexadecane, pentaerythrityl tetraisostearate, caprylic/capric triglyceride, canola oil, sunflower oil (*Helianthus annuus*), olive oil (*Olea europea*), cottonseed oil (*Gossypium herbaceum*), jojoba oil (*Simmondsia chinensis*), shea butter (*Butyrospermum parkii*), cocoa butter (*Theobroma cacao*), cupuacu butter (*Theobroma grandiflorum*), avocado oil (*Persea gratissima*), liquid paraffin, dimethicone, phenyl trimethicone, cyclopentasiloxane, dimethiconol and petrolatum.

c) Surfactants—anionic surfactants, eg sodium lauryl sulphate, sodium laureth sulphate, ammonium laureth sulphate, disodium laureth sulfosuccinate and sodium C12-15 pareth sulphate; amphoteric/zwitterionic surfactants, eg cocamidopropyl betaine, sodium cocoamphoacetate and cocamidopropyl hydroxysultaine; nonionic surfactants, eg laureth-3, oleth-5, cocamide DEA, cocamide MEA, PEG-5 cocamide, polysorbate 20, PEG-40 hydrogenated castor oil; and cationic surfactants, eg cetrimonium chloride, behentrimonium chloride and benzalkonium chloride.

d) Emulsifiers, eg steareth-2, steareth-21, steareth-10, ceteareth-5, ceteareth-12, ceteareth-20, cetearyl glucoside, oleth-10, glyceryl stearate, polyglyceryl-3 oleate, polyglyceryl-3 methylglucose distearate, sodium cetearyl sulphate, sodium stearate, PEG-12 Oleate, PEG-2 stearate, PEG-12 stearate, PEG-80 sorbitan, sorbitan oleate, sorbitan palmitate and cetyl PEG/PPG-10/1 dimethicone.

e) Chelating agents or sequestering agents (sequestrants)—ingredients that have the ability to complex with and inactivate metallic ions in order to prevent their adverse effects on the stability or appearance of the composition. Examples of chelating agents are ethylenediamine tetraacetic acid and its salts, notably the dipotassium and especially the disodium or tetrasodium salt.

f) Sunscreening agents—inorganic sunscreening agents, eg microfine titanium dioxide, microfine zinc oxide, iron oxides, talcs and boron nitride; and/or organic sunscreening agents, eg p-aminobenzoic acids, esters and derivatives thereof, for example, 2-ethylhexyl p-dimethyl-aminobenzoate and the octyl ester of p-aminobenzoic acid; methoxycinnamate esters such as 2-ethylhexyl p-methoxycinnamate, 2-ethoxyethyl p-methoxycinnamate or $\alpha,\beta$-di-(p-methoxycinnamoyl)-$\alpha'$-(2-ethylhexanoyl)-glycerin; benzophenones such as oxybenzone; 2-phenylbenzimidazole-5-sulfonic acid and disodium phenyl dibenzimidazole tetrasulfonate and terphthalylidene dicamphor sulfonic acid; alkyl-$\beta,\beta$-diphenylacrylates for example alkyl $\alpha$-cyano-$\beta,\beta$-diphenylacrylates such as octocrylene; triazines such as 2,4,6-trianilino-(p-carbo-2-ethylhexyl-1'-oxy)-1,3,5 triazine and bis-ethylhexyloxyphenol methoxyphenyl triazine; camphor derivatives such as methylbenzylidene camphor; organic pigment sunscreening agents such as methylene bis-benzotriazole tetramethyl butylphenol; silicone derivatives such as drometrizole trisiloxane, benzylidene malonate polysiloxane and dimethicodiethyl benzal malonate, salicylates such as octyl salicylate.

g) Preservatives—ingredients which prevent or retard microbial growth and thus protect the composition from spoilage. Examples of preservatives include DMDM hydantoin, propylparaben, methylparaben, phenoxyethanol, sodium benzoate, bronopol, sodium dehydroacetate, polyhexamethylenebiguanide hydrochloride, isothiazolone and diazolidinylurea.

h) Perfumes and colourings.

Topical Administration to the Hair

The present invention can be delivered to hair via any of the conventional formulations known to those skilled in the art, such as shampoos, conditioners (both emulsion and non-emulsion types), lotions (including developing lotions), sprays, gels, waxes, serums, mousses, tonics etc. Of these types of formulation, the range of ingredients can be broad. Such ingredients are surfactants, conditioning agents, waxes, thickeners, preservatives, and resins, sequestering agents, slip aids, vitamins, gelling agents, pearlising agents, pH adjusting agents and sunscreening agents and colours.

The composition may include a surfactant such as cosmetically acceptable salts of alkyl ether sulphates (such as ammonium laureth sulphate or sodium laureth sulphate), alkyl and alkylamidoalkyl betaines (such as cocamidopropyl betaine), ethoxylated alcohols, polyethyleneglycol carboxylates, accepted salts of alkyl sulphates (such as ammonium lauryl sulphate or sodium lauryl sulphate), sulphosuccinates (such as disodium laureth sulphosuccinate), amphoacetates and amphodiacetates (such as disodium cocoamphodiacetates), alkylglucosides and alcohol sulphonates, incorporated in an amount of from about 1% to 99% by weight of the composition.

The composition may also include a thickener or viscosity controlling agent such as an amine oxide, block polymers of ethylene oxide and propylene oxide (for examples, those available from BASF Wyandotte under the trade name "Pluronic"®), ethoxylated fatty alcohols, cellulosic derivatives (such as hydroxypropylmethyl cellulose), salt (NaCl), phthalic acid amide, polyvinylalcohols and fatty alcohols, suitably in an amount from about 0.5% to about 10% by weight of the composition.

Sequestering agents may be added to the composition, such as ethylenediamine tetraacetic acid (EDTA) and salts thereof, suitably in an amount of from about 0.005% to about 0.5% by weight of the composition.

Also included in the composition may be oils and waxes such as cocoa butter, suitably in an amount of from about 0.01% to about 1.0% by weight of the composition.

The composition may also include gelling agents such as poly(methyl vinyl ether-co-maleic anhydride) (PVM/MA) or a decadiene crosspolymer (available under the trade name Stabileze® 06), suitably in an amount from about 0.1% to 2.0% by weight of the composition.

Pearlising agents may be included eg stearic monoethanolamine, suitably in an amount from about 0.01% to about 10% by weight of the composition. The pH of the composition is generally required to be in the range of 8 to 12, preferably in the range of 9-10.5, for the desired performance as a permanent hair colour. To achieve this, the composition may need to be buffered using means well known in the art, such as a system comprising succinic acid, citric acid, lactic acid and acceptable salts thereof, phosphoric acid, mono- or disodium phosphate and sodium carbonate. The pH may be adjusted with an agent such as sodium hydroxide, aminomethyl propanol, triethanolamine and caustic potash, suitably in an amount from about 0.01% to about 10% by weight of the composition.

If the composition is in the form of an emulsion, the emulsifiers used may be any emulsifiers known in the art for use in water-in-oil or oil-in-water emulsions, examples of which follow:
a) sesquioleates such as sorbitan sesquioleate, available commercially for example under the trade name Arlacel 83 (ICI), or polyglyceryl-2-sesquioleate;
b) ethoxylated esters of derivatives of natural oils such as the polyethoxylated ester of hydrogenated castor oil available commercially for example under the trade name Arlacel 989 (ICI);
c) silicone emulsifiers such as silicone polyols available commercially for example under the trade name Dow Corning 5225C (Dow Corning) and Abil WE09 (Goldschmidt);
d) anionic emulsifiers such as fatty acid soaps eg potassium stearate and fatty acid sulphates eg sodium cetostearyl sulphate available commercially under the trade name Dehydag (Henkel);
e) ethoxylated fatty alcohols, for example the emulsifiers available commercially under the trade name Brij (ICI);
f) sorbitan esters, for example the emulsifiers available commercially under the trade name Span (ICI);
g) ethoxylated sorbitan esters, for example the emulsifiers available commercially under the trade name Tween (ICI);
h) ethoxylated fatty acid esters such as ethoxylated stearates, for example the emulsifiers available commercially under the trade name Myrj (ICI);
i) ethoxylated mono-, di-, and tri-glycerides, for example the emulsifiers available commercially under the trade name Labrafil (Alfa Chem.);
j) non-ionic self-emulsifying waxes, for example the wax available commercially under the trade name Polawax (Croda);
k) ethoxylated fatty acids, for example the emulsifiers available commercially under the trade name Tefose (Alfa Chem.); or
l) mixtures thereof.

The amount of emulsifier present in the water-in-oil compositions of the present invention is preferably in the range 0.1 to 10%.

Oral Administration

For oral administration, the active ingredient may be incorporated in a variety of dosage forms. Preferably, the active ingredient will be formulated and administered as a solid dosage form, most commonly as a tablet or the like. Other solid dosage forms include capsules, lozenges, powders and granules, and formulations such as a syrup (solution or suspension) may also be possible, as may other dosage forms.

For formulation in the presently preferred form for oral administration, ie as a tablet, the active ingredient will generally be combined with various excipients in a manner which is known per se. In particular, the tablet will generally comprise one or more diluents or bulking agents. A lubricant may also be included to facilitate release of the formed tablets from the tableting dies of a tablet forming machine.

Preferred materials for the diluent or bulking agents include calcium carbonate, polysaccharides and derivatives thereof, and saccharides.

Polysaccharides which may be used include starch, eg maize starch, cellulose, eg powdered cellulose and microcrystalline cellulose, water-insoluble modified starches, eg sodium carboxymethyl starch, water-insoluble cellulose derivatives, eg croscarmellose sodium (cross-linked sodium carboxymethyl cellulose), cross-linked polyvinylpyrrolidone and alginic acid.

Another preferred form of diluent is a saccharide. Suitable saccharides include, for example, sucrose, lactose, dextrose, sorbitol and xylitol.

Particularly preferred diluents are microcrystalline cellulose, eg the products sold as Avicel PH-101 and Avicel PH-102 (Avicel is a Trade Mark) by the FMC Corporation of Philadelphia, Pa., USA, and lactose.

The lubricant may be, for example, stearic acid, a metallic stearate, a polyethylene glycol of molecular weight of 4,000 or more, or purified talc. The preferred lubricant is a metallic stearate, particularly magnesium stearate.

Other additional excipients may be included. Typical examples include flow aids, eg fused silica compounds, and disintegrants, including sodium starch glycolate, starch and crosscarmellose sodium.

The tablet formulation may be prepared by methods that are familiar to those skilled in the art, eg processes involving wet or dry granulation or direct compression into a tablet without an intermediate, eg a wet or dry granulation, stage.

Test Methods

The effectiveness of the antioxidant combinations of the present invention may be demonstrated by any suitable in vitro and in vivo test methods. Examples of currently available methods include the ABEL® antioxidant assay, and assays based on skin models, such as the EpiStem Human Skin Equivalent Model, and the Schrader assay.

ABEL® Antioxidant Assay

The ABEL antioxidant assay is an in vitro assay for testing the antioxidant capacity of a material. It utilises a photoprotein, which emits light when challenged with various free radical species, eg peroxynitrite, hydroxyl radicals or halogenated oxidants.

If a material is challenged with one or more of these free radical species, then any antioxidant in the sample will compete with the photoprotein. The result of this competition is a reduction in the amount of light emitted and sometimes, in addition, a delay in the time at which the maximum light emitted occurs. A light response curve can be produced for each sample tested, and $EC_{50}$ and ABEL-RAC values calculated. The $EC_{50}$ (effective concentration) is the concentration (normalised to g/L or mg/mL) of a material that reduces the light emitted by 50%. This reduction in light is a measure of the antioxidant capacity of the test material. The reciprocal of the $EC_{50}$ values multiplied by 100 is referred to as the ABEL-RAC score.

The ABEL® antioxidant assay with peroxynitrite is the assay of choice to assess total antioxidant capacity because peroxynitrite attacks almost all compounds, including hydrophobic and hydrophilic antioxidants. Pro-oxidants are also identified with the peroxynitrite assay. Other ABEL® antioxidant assays use superoxide (produced as a single bolus in high concentration as well as enzymatically), hydroxyl radical and hyperchlorous acid (the halogenated oxidant assay).

Pro-oxidants are not observed with the hydroxyl radical and halogenated oxidant assays. The hydroxyl radical assay is recommended when samples are water-soluble and the halogenated assay when the samples are soluble in organic solvent. This is because solvents such as ethanol, methanol, acetone and DMSO are good quenchers of hydroxyl radicals, and therefore the organic solvents contribute to the antioxidant effect shown by the sample. Organic solvents have little effect, however, on the halogenated oxidant assay.

EpiStem Human Skin Equivalent Model

The EpiStem Human Skin Equivalent Model (DERMO-QUANT®) is a highly differentiated in vitro skin equivalent model that is used to assess the efficacy and mode of action of novel agents. The model is generated from primary human keratinocytes on a collagen gel substrate containing human dermal fibroblasts. It is grown at the air-liquid interface which allows full epidermal stratification and epidermal interactions to occur.

Schrader Assay

This is a commercial assay in which the test product is applied to the forearms of volunteers over a 2 week period and tape strips are taken. The antioxidant activity of the tape-strips is measured using a chemiluminescence method.

BRIEF DESCRIPTION OF DRAWINGS

FIGS. 1 to 10 show the results of ABEL® peroxynitrite antioxidant assays for combinations of three antioxidant agents referred to as combinations 1 to 10 respectively.

FIGS. 11 to 15 show the results of further ABEL® peroxynitrite antioxidant assays for combinations 1, 3, 4, 8 and 9 respectively.

FIGS. 16 to 18 show the results of ABEL® peroxynitrite antioxidant assays for a cream containing combinations of three antioxidant agents, viz combinations 1, 8 and 8 mod respectively.

FIG. 20 shows the results of the ABEL® peroxynitrite assay for a cream containing a further combination of three antioxidant agents, referred to as combination 12.

DETAILED DESCRIPTION

Figure 2:
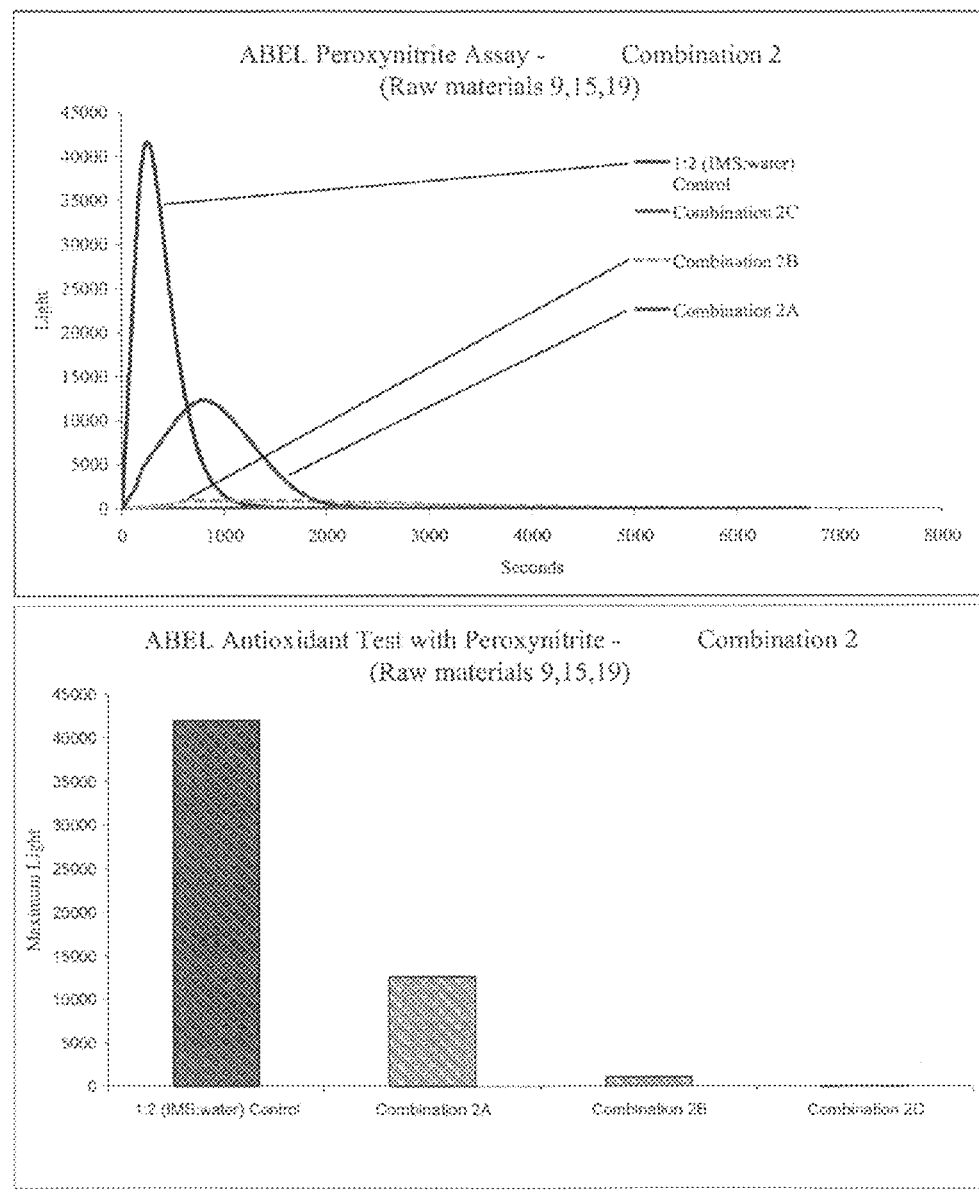
Figure 3:
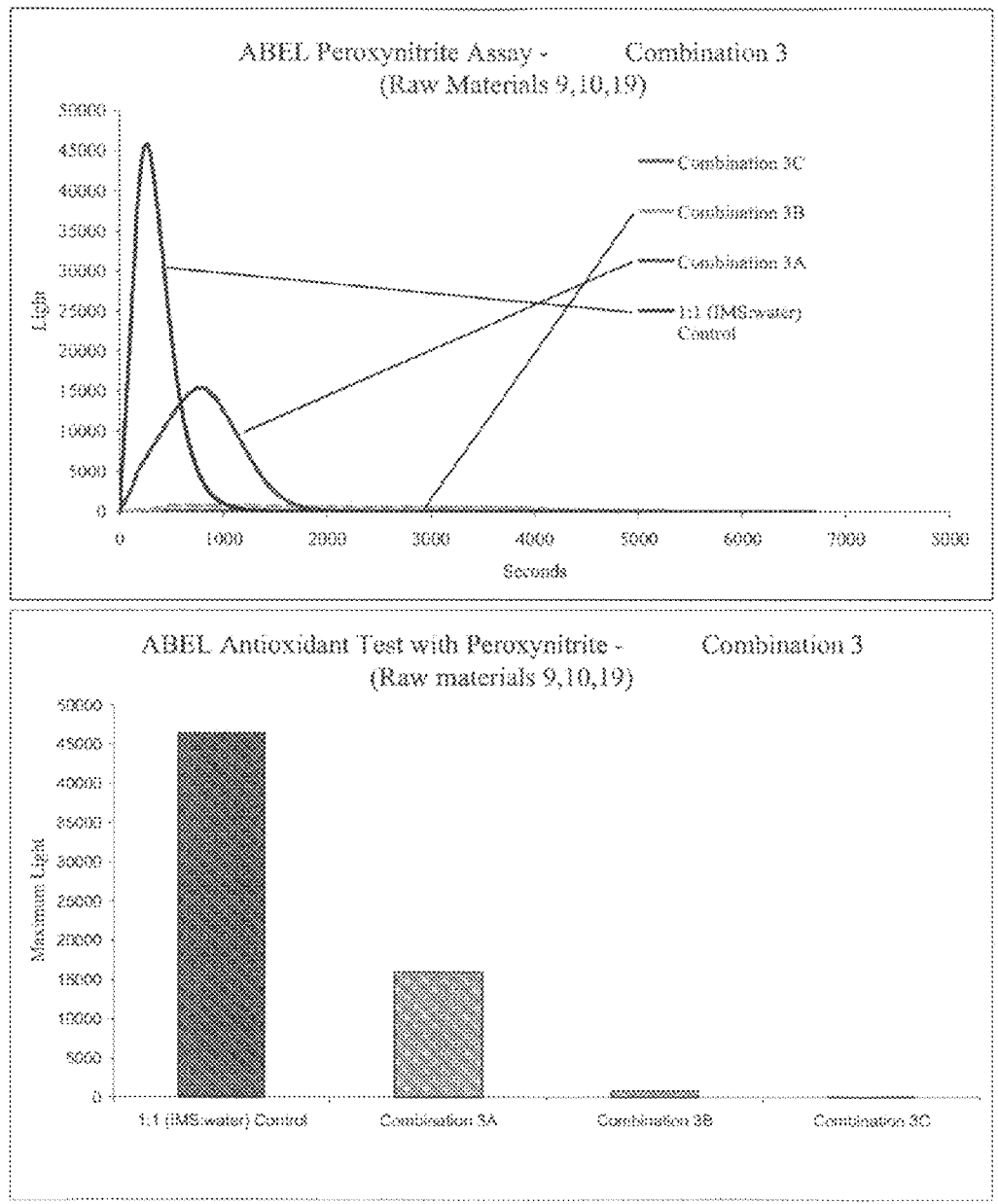
Figure 4:
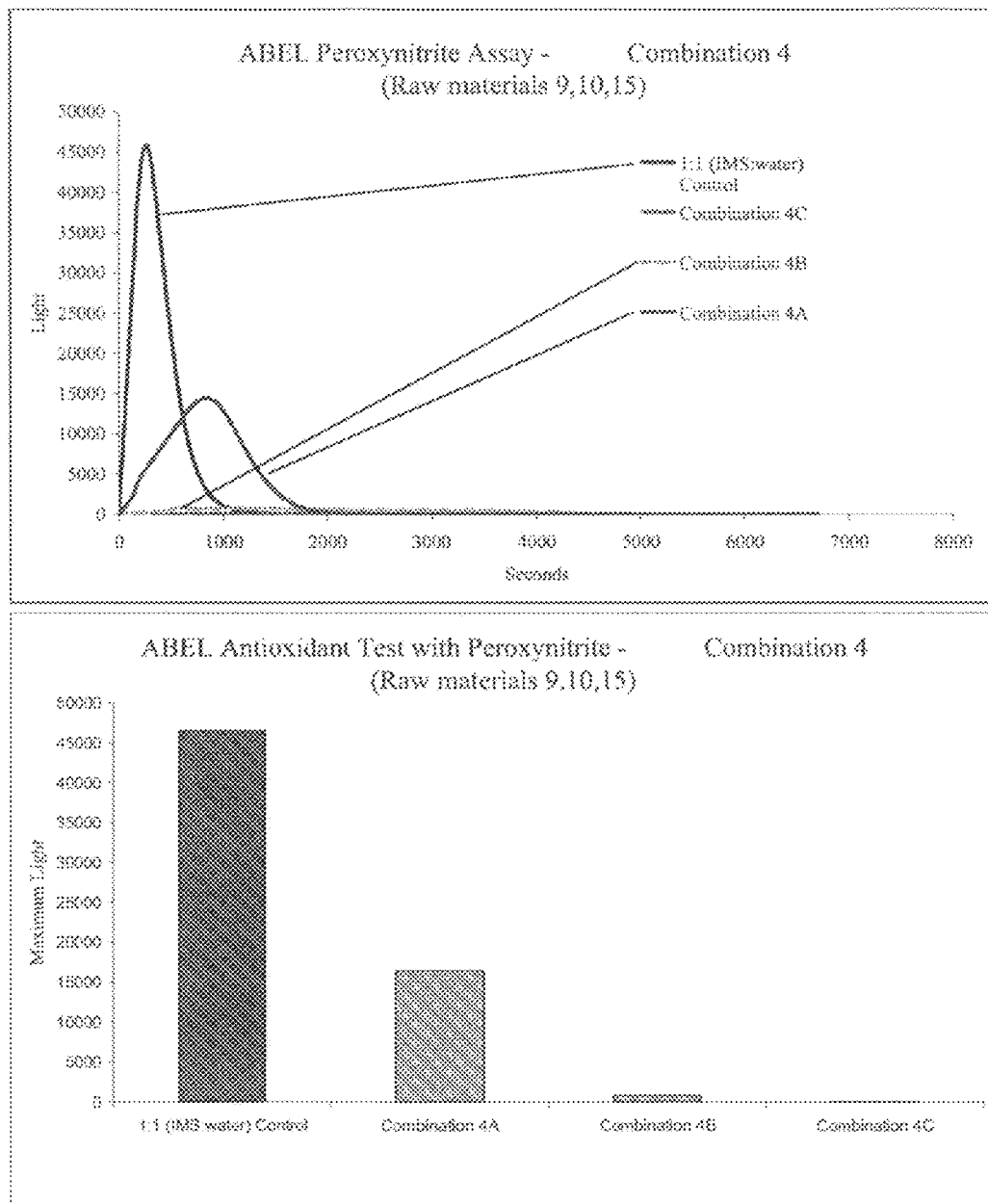
Figure 5:
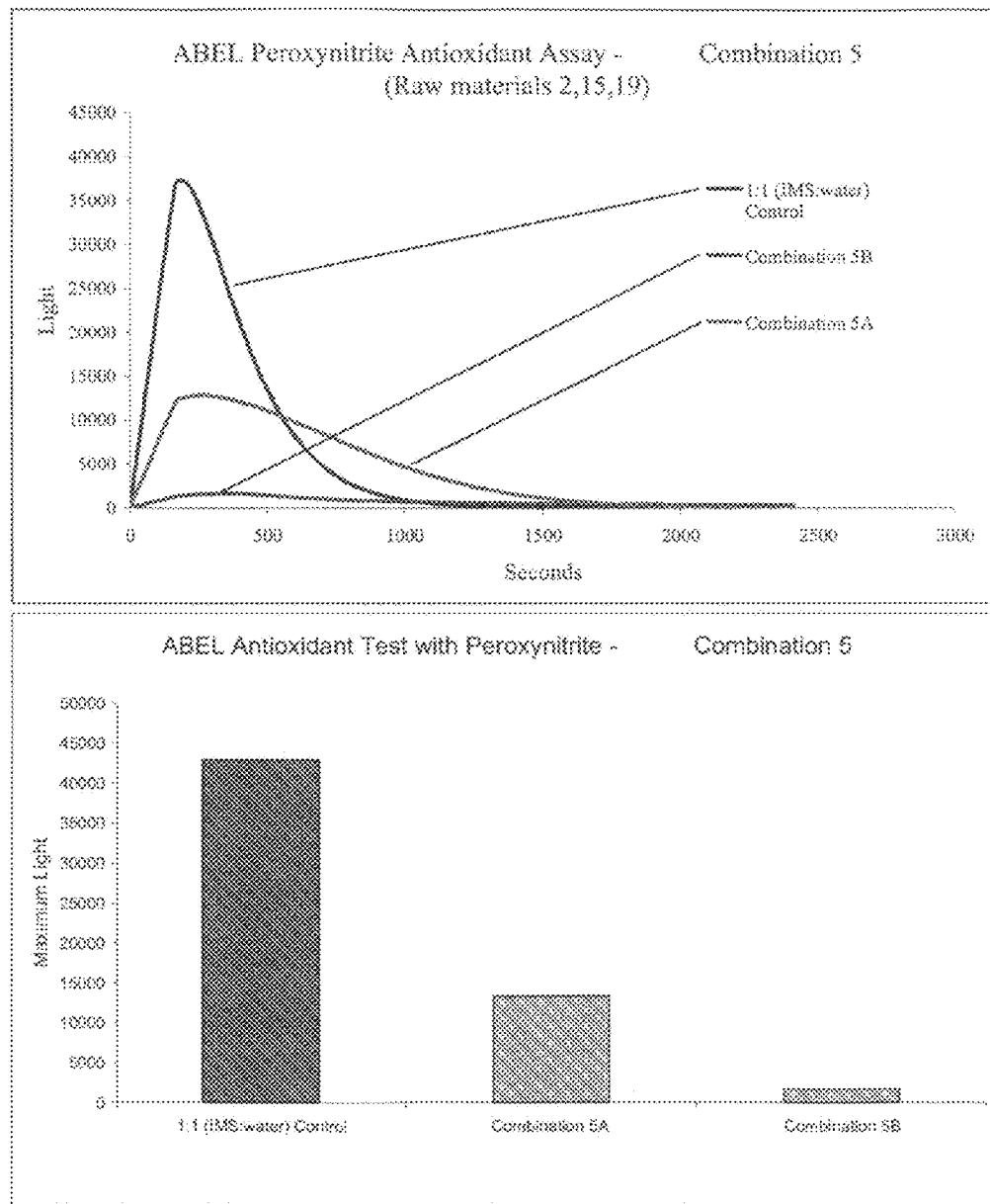
Figure 6:
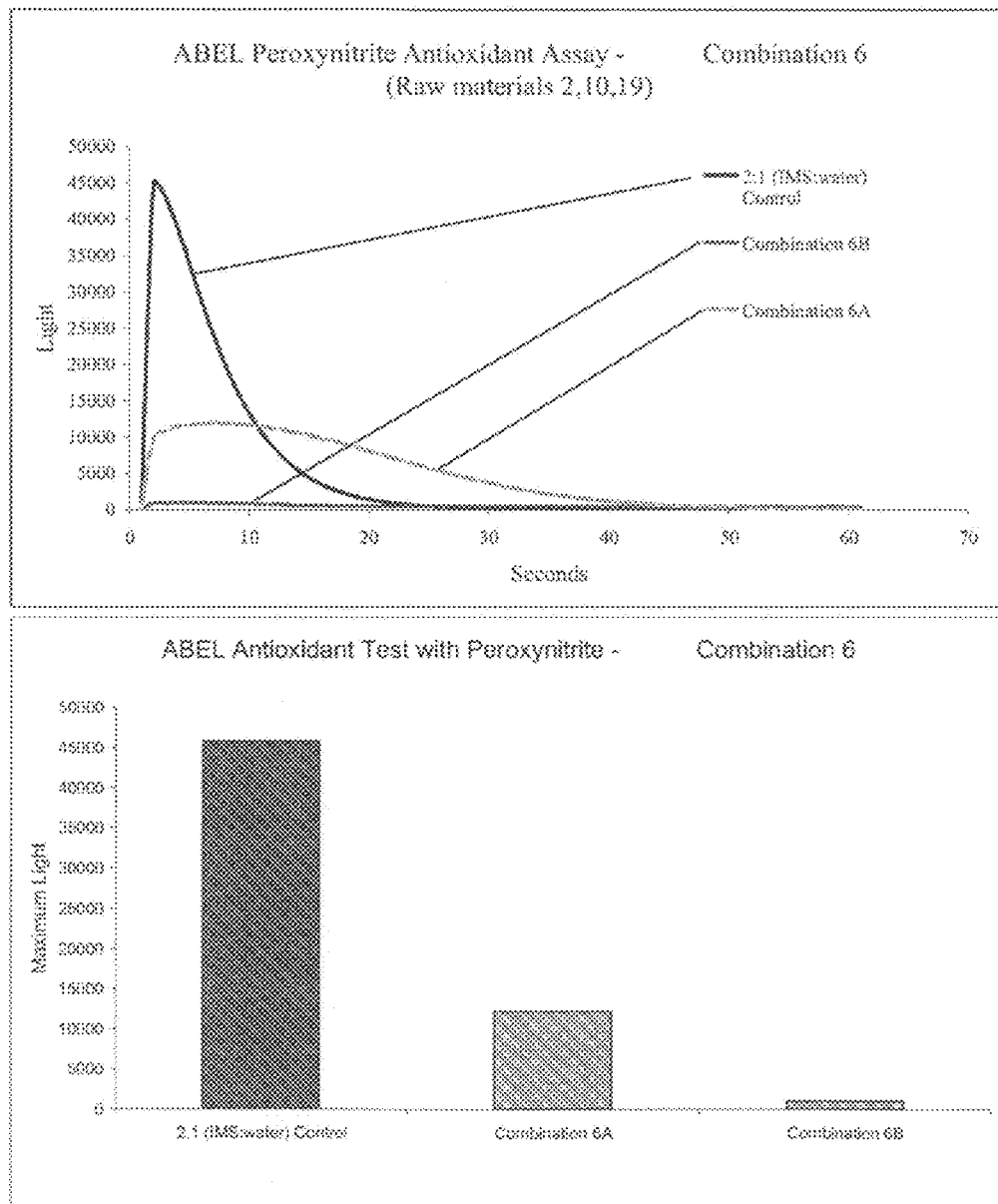
Figure 7:
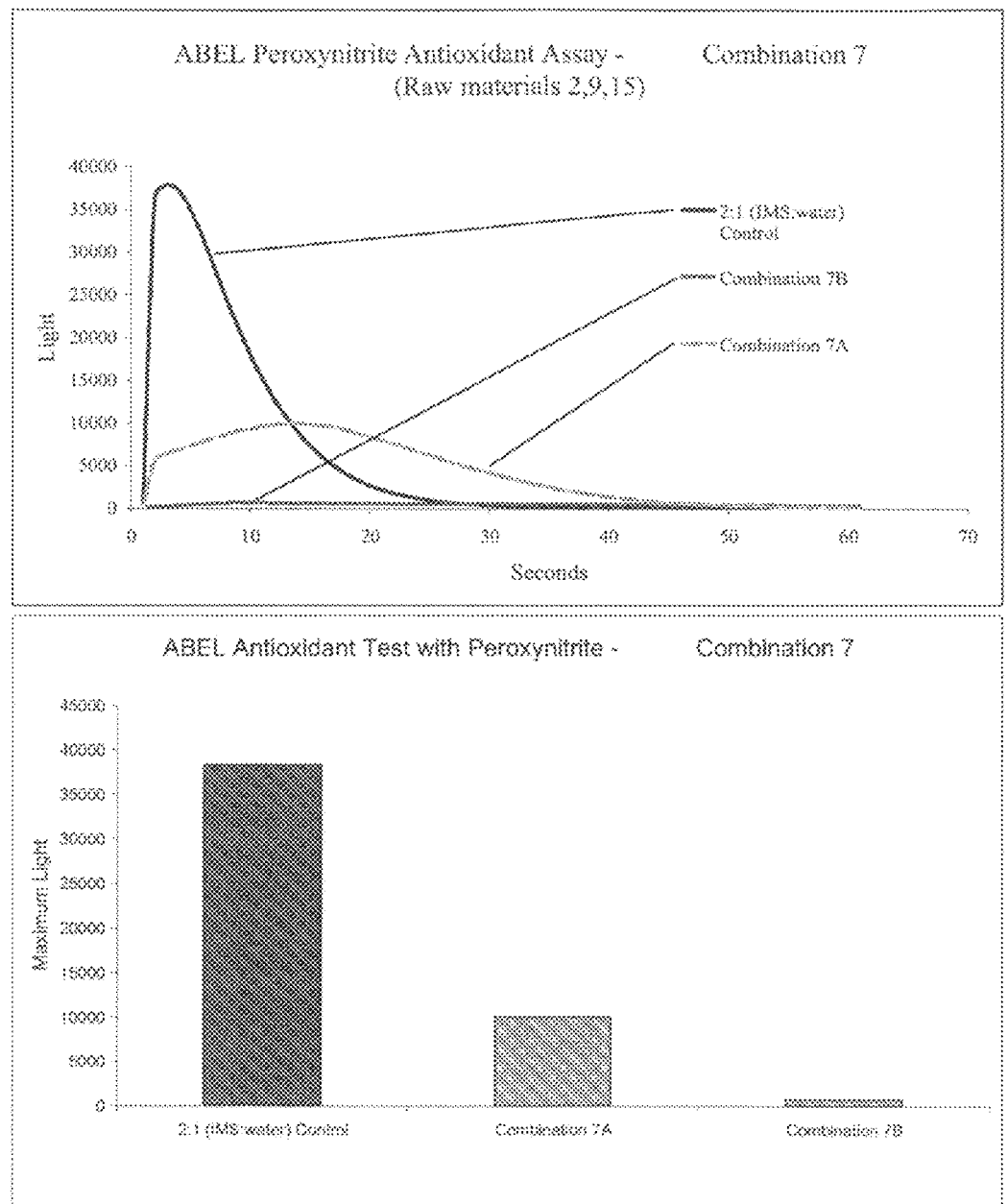
Figure 8:
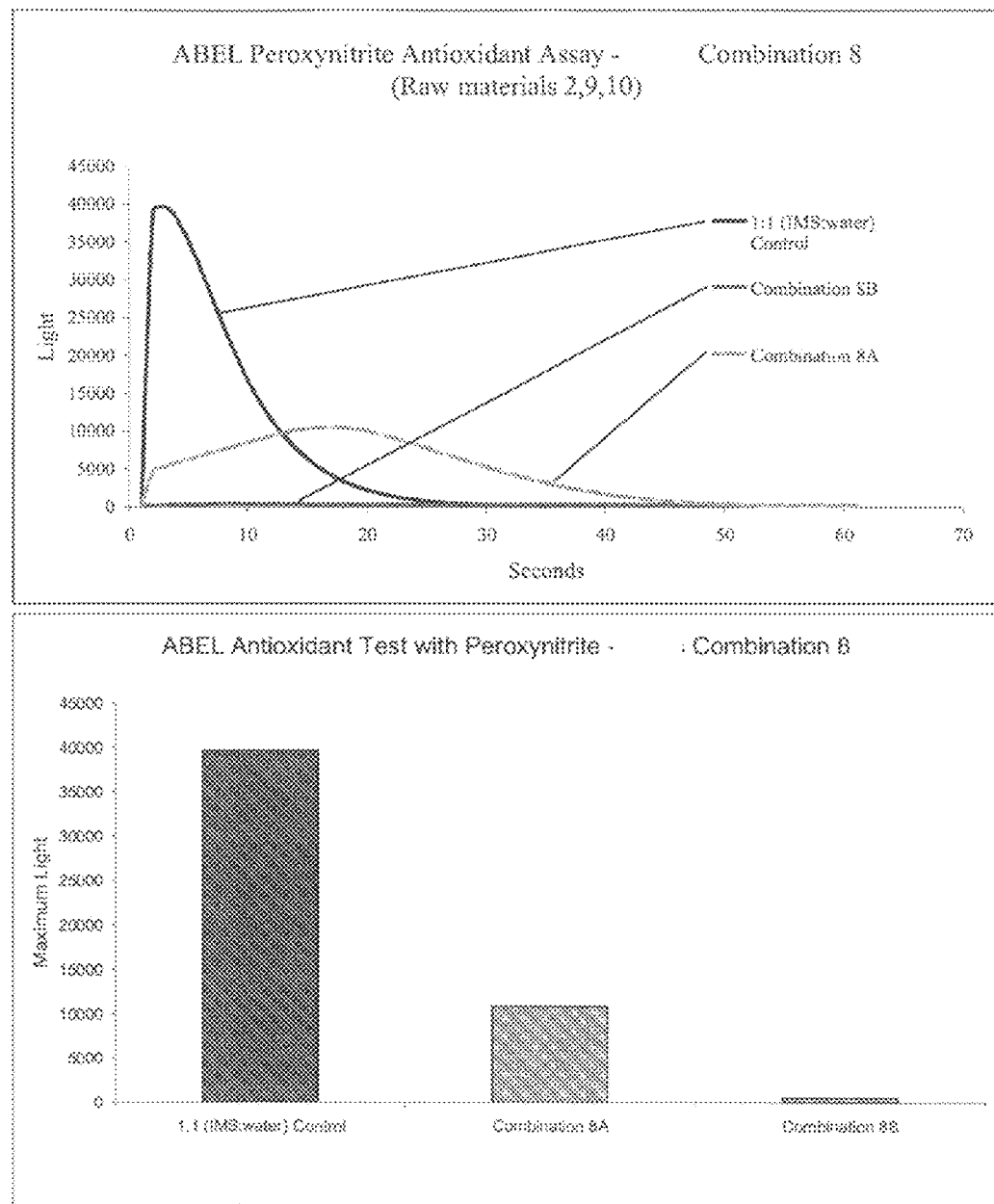
Figure 9:
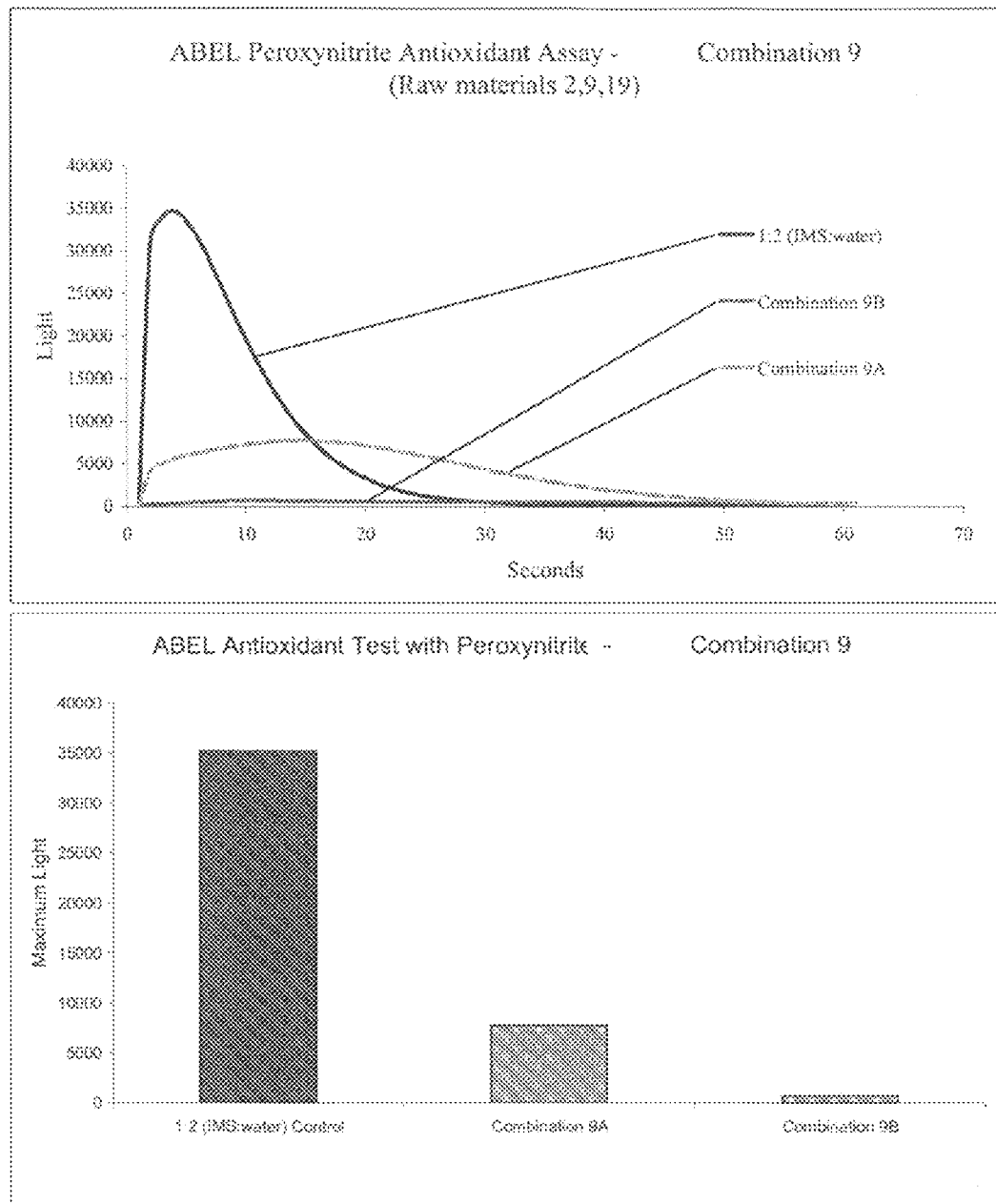
Figure 10:
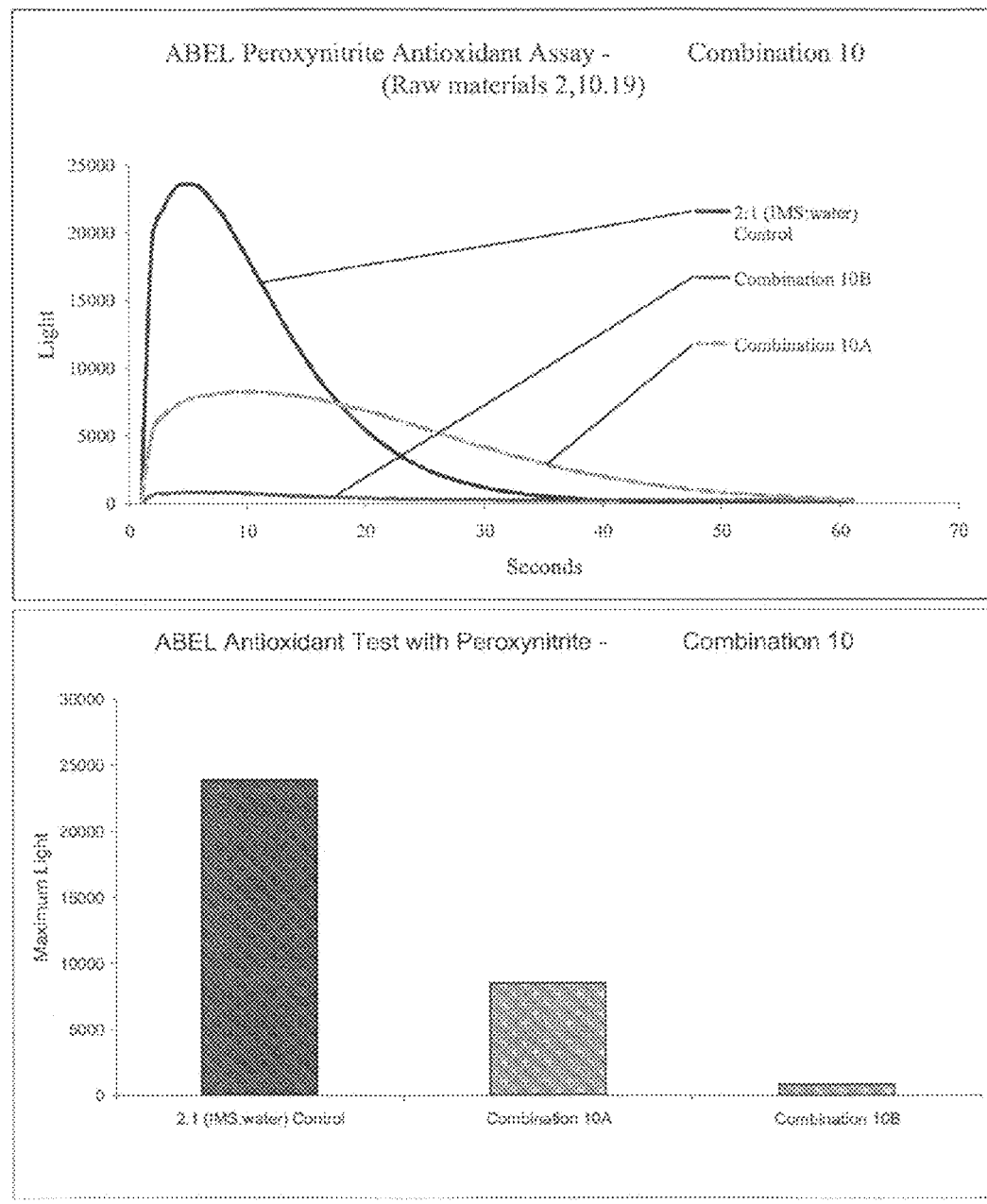
Figure 15:
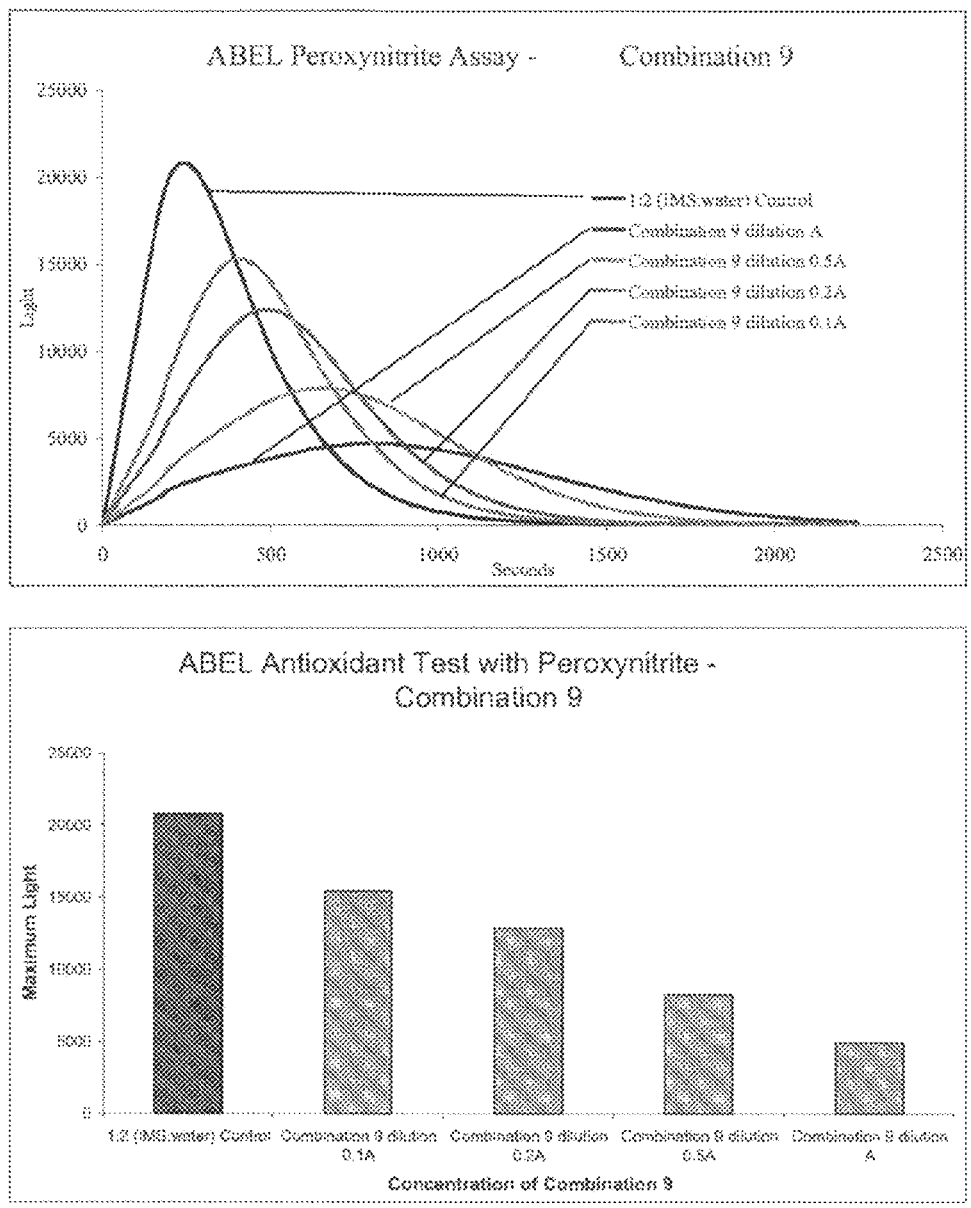

The invention will now be described in greater detail, by way of illustration only, with reference to the following Examples. Examples 1-28 provide example formulations, and Examples 29-34 describe the results of in vitro testing using the ABEL® peroxynitrite antioxidant assay.

Example 1

Skin Cream

| Material | % w/w |
| --- | --- |
| Paraffinum liquidum | 10 |
| Cetearyl alcohol | 2 |
| Glycerin | 2 |
| Glyceryl stearate | 2 |
| Cetyl alcohol | 2 |
| PEG-100 stearate | 2 |
| Dimethicone | 1.5 |
| PEG-20 stearate | 0.5 |
| Phenoxyethanol | 0.4 |
| Carbomer | 0.2 |
| Methylparaben | 0.2 |
| Propylparaben | 0.15 |
| Potassium hydroxide | 0.06 |
| Potassium hydroxide | 0.015 |
| Alcohol denat. | 0.5 |
| Tetrasodium EDTA | 0.05 |
| Ascorbyl glucoside | 0.05 |
| *Ginkgo* extract | 0.005 |
| *Emblica* extract | 0.015 |
| Dimethylmethoxy chromanol | 0.02 |
| White lupin peptides | 1 |
| Palmitoyl oligopeptide and Palmitoyl tetrapeptides | 1.5 |
| Retinyl palmitate | 0.07 |
| Aqua | To 100 |

Method of Manufacture

1. To water add and dissolve tetrasodium EDTA.
2. Using homogenisation sprinkle in carbomer and continue to homogenise for 5 minutes or until hydrated.
3. Add methylparaben and heat up to 70-75° C.
4. In a separate vessel weigh out oil phase and heat to 70-75° C. (Paraffin liquidum, cetearyl alcohol, glyceryl stearate, cetyl alcohol, PEG-100 stearate, dimethicone, PEG-20 stearate, phenoxyethanol, retinyl palmitate and propylparaben.)
5. With both phases at 70-75° C. add the oil phase to the water phase and homogenise for 2 minutes.
6. Add potassium hydroxide and homogenise for 2 minutes.
7. Cool to room temperature.
8. Dissolve ascorbyl glucoside in 2% water, neutralise with potassium hydroxide and stir into bulk.
9. Dissolve ginkgo extract in glycerin and stir into bulk.
10. Dissolve emblica extract in 2% water and stir into bulk.
11. Dissolve dimethylmethoxy chromanol in alcohol denat. and stir into bulk.
12. Stir into bulk white lupin peptides, palmitoyl oligopeptide and palmitoyl tetrapeptides
13. Make to weight with water and stir smooth.

Example 2

Skin Cream

| Material | % w/w |
| --- | --- |
| Paraffinum liquidum | 10 |
| Cetearyl alcohol | 2 |
| Glycerin | 2 |
| Steareth-21 | 2.94 |
| Steareth-2 | 2 |
| Cetyl alcohol | 2 |
| Dimethicone | 1.5 |
| Phenoxyethanol | 0.4 |
| Carbomer | 0.2 |
| Methylparaben | 0.2 |
| Ethylparaben | 0.1 |
| Potassium hydroxide | 0.06 |
| Alcohol denat. | 0.5 |
| Tetrasodium EDTA | 0.05 |
| Sodium ascorbyl phosphate | 0.05 |
| *Ginkgo* extract | 0.005 |
| *Emblica* extract | 0.015 |
| Dimethylmethoxy chromanol | 0.02 |

-continued

| Material | % w/w |
|---|---|
| White lupin peptides | 1 |
| Palmitoyl oligopeptide and Palmitoyl tetrapeptides | 1.5 |
| Retinyl palmitate | 0.07 |
| Aqua | To 100 |

Method of Manufacture
1. To water add and dissolve tetrasodium EDTA.
2. Using homogenisation sprinkle in carbomer and continue to homogenise for 5 minutes or until hydrated.
3. Add methylparaben and heat up to 70-75° C.
4. In a separate vessel weigh out oil phase and heat to 70-75° C. (Paraffin liquidum, cetearyl alcohol, steareth-21, steareth-2, cetyl alcohol, dimethicone, phenoxyethanol and retinyl palmitate)
5. With both phases at 70-75° C. add the oil phase to the water phase and homogenise for 2 minutes.
6. Add potassium hydroxide and homogenise for 2 minutes.
14. Cool to room temperature.
15. Dissolve sodium ascorbyl phosphate in 2% water and stir into bulk.
16. Dissolve ginkgo extract in glycerin and stir into bulk.
17. Dissolve emblica extract in 2% water and stir into bulk.
18. Dissolve dimethylmethoxy chromanol in alcohol denat. and stir into bulk.
19. Stir into bulk white lupin peptides, palmitoyl oligopeptide and palmitoyl tetrapeptides
20. Make to weight with water and stir smooth.

Example 3

Skin Cream with SPF

| Material | % w/w |
|---|---|
| C12-15 alkyl benzoate | 5 |
| Butyl methoxydibenzoylmethane | 3 |
| Ethylhexyl methoxycinnamate | 5 |
| Cetearyl alcohol | 2 |
| Glycerin | 2 |
| Glyceryl stearate | 2 |
| Cetyl alcohol | 2 |
| PEG-100 stearate | 2 |
| Dimethicone | 1.5 |
| PEG-20 stearate | 0.5 |
| Phenoxyethanol | 0.4 |
| Carbomer | 0.2 |
| Methylparaben | 0.2 |
| Propylparaben | 0.15 |
| Potassium hydroxide | 0.06 |
| Potassium hydroxide | 0.015 |
| Alcohol denat. | 0.5 |
| Tetrasodium EDTA | 0.05 |
| Ascorbyl glucoside | 0.05 |
| *Ginkgo* extract | 0.005 |
| *Emblica* extract | 0.015 |
| Dimethylmethoxy chromanol | 0.02 |
| White lupin peptides | 1 |
| Palmitoyl oligopeptide and Palmitoyl tetrapeptides | 1.5 |
| Retinyl palmitate | 0.07 |
| Aqua | To 100 |

Method of Manufacture
1. To water add and dissolve tetrasodium EDTA.
2. Using homogenisation sprinkle in carbomer and continue to homogenise for 5 minutes or until hydrated.
3. Add methylparaben and heat up to 70-75° C.
4. In a separate vessel weigh out oil phase and heat to 70-75° C. (C12-15 alkyl benzoate, butyl methoxydibenzoylmethane, ethylhexyl methoxydibenzoylmethane, cetearyl alcohol, glyceryl stearate, cetyl alcohol, PEG-100 stearate, dimethicone, PEG-20 stearate, phenoxyethanol, retinyl palmitate and propylparaben)
5. With both phases at 70-75° C. add the oil phase to the water phase and homogenise for 2 minutes.
6. Add potassium hydroxide and homogenise for 2 minutes.
7. Cool to room temperature.
8. Dissolve ascorbyl glucoside in 2% water, neutralise with potassium hydroxide and stir into bulk.
9. Dissolve ginkgo extract in glycerin and stir into bulk.
10. Dissolve emblica extract in 2% water and stir into bulk.
11. Dissolve dimethylmethoxy chromanol in alcohol denat. and stir into bulk.
12. Stir into bulk White lupin peptides, palmitoyl oligopeptide and palmitoyl tetrapeptides
13. Make to weight with water and stir smooth.

Example 4

Gel

| Material | % w/w |
|---|---|
| Glycerin | 3 |
| Acrylates/C10-30 alkyl acrylate crosspolymer | 1 |
| Alcohol denat. | 0.5 |
| Phenoxyethanol | 0.4 |
| Potassium hydroxide | 0.29 |
| Potassium hydroxide | 0.015 |
| Tetrasodium EDTA | 0.05 |
| Methylparaben | 0.08 |
| Ethylparaben | 0.05 |
| Ascorbyl glucoside | 0.05 |
| *Ginkgo* extract | 0.005 |
| *Emblica* extract | 0.015 |
| Dimethylmethoxy chromanol | 0.02 |
| White lupin peptides | 1 |
| Palmitoyl oligopeptide and Palmitoyl tetrapeptides | 1.5 |
| Retinyl palmitate | 0.07 |
| Aqua | To 100 |

Method of Manufacture
1. To water add and dissolve tetrasodium EDTA.
2. Using homogenisation sprinkle in acrylates/C10-30 alkyl acrylate crosspolymer and continue to homogenise for 5 minutes or until hydrated.
3. Stir in potassium hydroxide to form gel.
4. Dissolve ascorbyl glucoside in 2% water, neutralise with potassium hydroxide and stir into bulk.
5. Dissolve ginkgo extract in glycerin and stir into bulk.
6. Dissolve emblica extract in 2% water and stir into bulk.
7. Dissolve dimethylmethoxy chromanol and retinyl palmitate in alcohol denat. and stir into bulk.
8. Stir into bulk white lupin peptides, palmitoyl oligopeptide and palmitoyl tetrapeptides
9. Make to weight with water and stir smooth.
10. Mix together phenoxyethanol, methylparaben and ethylparaben. Heat until a clear solution is formed. Stir into main vessel.
11. Make to weight with water and stir smooth.

Example 5

Gel

| Material | % w/w |
| --- | --- |
| Glycerin | 3 |
| Acrylates/C10-30 alkyl acrylate crosspolymer | 1 |
| Alcohol denat. | 0.5 |
| Phenoxyethanol | 0.4 |
| Potassium hydroxide | 0.29 |
| Potassium hydroxide | 0.015 |
| Tetrasodium EDTA | 0.05 |
| Methylparaben | 0.08 |
| Ethylparaben | 0.05 |
| Ascorbyl glucoside | 0.05 |
| *Ginkgo* extract | 0.018 |
| *Emblica* extract | 0.013 |
| Dimethylmethoxy chromanol | 0.0018 |
| White lupin peptides | 1 |
| Palmitoyl oligopeptide and Palmitoyl tetrapeptides | 1.5 |
| Retinyl palmitate | 0.07 |
| Aqua | To 100 |

Method of Manufacture
1. To water add and dissolve tetrasodium EDTA.
2. Using homogenisation sprinkle in acrylates/C10-30 alkyl acrylate crosspolymer and continue to homogenise for 5 minutes or until hydrated.
3. Stir in potassium hydroxide to form gel.
4. Dissolve ascorbyl glucoside in 2% water, neutralise with potassium hydroxide and stir into bulk.
5. Dissolve ginkgo extract in glycerin and stir into bulk.
6. Dissolve emblica extract in 2% water and stir into bulk.
7. Dissolve dimethylmethoxy chromanol and retinyl palmitate in Alcohol denat. and stir into bulk.
8. Stir into bulk white lupin peptides, palmitoyl oligopeptide and palmitoyl tetrapeptides
9. Make to weight with water and stir smooth.
10. Mix together phenoxyethanol, methylparaben and ethylparaben. Heat until a clear solution is formed. Stir into main vessel.
11. Make to weight with water and stir smooth.

Example 6

Water-in-Oil Emulsion

| Material | % w/w |
| --- | --- |
| Paraffinum liquidum | 8 |
| Ethylhexyl stearate | 7 |
| Isopropyl myristate | 5 |
| Glycerin | 3 |
| Polyglyceryl-3 oleate | 1.7 |
| Butylene glycol | 1.4 |
| Cetyl PEG/PPG-10/1 dimethicone | 1.3 |
| Sodium chloride | 0.75 |
| Magnesium sulfate | 0.75 |
| Phenoxyethanol | 0.7 |
| Methylparaben | 0.2 |
| Ethylparaben | 0.1 |
| Ascorbyl glucoside | 0.05 |
| Potassium hydroxide | 0.015 |
| *Ginkgo* extract | 0.005 |
| *Emblica* extract | 0.015 |
| Dimethylmethoxy chromanol | 0.02 |
| Alcohol denat. | 0.5 |
| White lupin peptides | 2 |
| Palmitoyl oligopeptide and Palmitoyl tetrapeptides | 3 |
| Retinyl palmitate | 0.07 |
| Aqua | To 100 |

Method of Manufacture
1. In the main vessel add paraffin liquidum, ethylhexyl stearate, isopropyl myristate, polyglyceryl-3 oleate, cetyl PEG/PPG-10/1 dimethicone and retinyl palmitate.
2. Separately weigh out water, sodium chloride, magnesium sulfate, butylene glycol.
3. Separately mix together phenoxyethanol, methylparaben and ethylparaben. Heat until dissolved and add to the water phase.
4. Add the water phase to the oil phase slowly with constant stirring at high speed. Continue stirring for 5 minutes.
5. Dissolve ascorbyl glucoside in 2% water, neutralise with potassium hydroxide and stir into bulk.
6. Dissolve ginkgo extract in glycerin and stir into bulk.
7. Dissolve emblica extract in 2% water and stir into bulk.
8. Dissolve dimethylmethoxy chromanol in alcohol denat. and stir into bulk.
12. Stir into bulk white lupin peptides, palmitoyl oligopeptide and palmitoyl tetrapeptides.
13. Homogenise the product for 5 minutes at 3500 rpm.

Example 7

Water-in-Oil Emulsion

| Material | % w/w |
| --- | --- |
| Paraffinum liquidum | 8 |
| Ethylhexyl stearate | 7 |
| Isopropyl myristate | 5 |
| Glycerin | 3 |
| Polyglyceryl-3 oleate | 1.7 |
| Butylene glycol | 1.4 |
| Cetyl PEG/PPG-10/1 dimethicone | 1.3 |
| Sodium chloride | 0.75 |
| Magnesium sulfate | 0.75 |
| Phenoxyethanol | 0.7 |
| Methylparaben | 0.2 |
| Ethylparaben | 0.1 |
| Ascorbyl glucoside | 0.05 |
| Potassium hydroxide | 0.015 |
| Alcohol denat. | 0.5 |
| *Ginkgo* extract | 0.018 |
| *Emblica* extract | 0.013 |
| Dimethylmethoxy chromanol | 0.001 |
| White lupin peptides | 1 |
| Palmitoyl oligopeptide and Palmitoyl tetrapeptides | 1.5 |
| Retinyl palmitate | 0.07 |
| Aqua | To 100 |

Method of Manufacture
1. In the main vessel add paraffin liquidum, ethylhexyl stearate, isopropyl myristate, polyglyceryl-3 oleate, cetyl PEG/PPG-10/1 dimethicone and retinyl palmitate.
2. Separately weigh out water, sodium chloride, magnesium sulfate, butylene glycol.

3. Separately mix together phenoxyethanol, methylparaben and ethylparaben. Heat until dissolved and add to the water phase.
4. Add the water phase to the oil phase slowly with constant stirring at high speed. Continue stirring for 5 minutes.
5. Dissolve ascorbyl glucoside in 2% water, neutralise with potassium hydroxide and stir into bulk.
6. Dissolve ginkgo extract in glycerin and stir into bulk.
7. Dissolve emblica extract in 2% water and stir into bulk.
8. Dissolve dimethylmethoxy chromanol in alcohol denat. and stir into bulk.
9. Stir into bulk white lupin peptides, palmitoyl oligopeptide and palmitoyl tetrapeptides.
10. Homogenise the product for 5 minutes at 3500 rpm.

Example 8

Hair Conditioner

| Material | % w/w |
| --- | --- |
| Cetyl alcohol | 4 |
| Cetrimonium chloride | 3 |
| Phenoxyethanol | 0.6 |
| Glycerin | 2 |
| Alcohol denat. | 0.5 |
| Ginkgo extract | 0.018 |
| Emblica extract | 0.013 |
| Dimethylmethoxy chromanol | 0.0018 |
| Aqua | To 100 |

Method of Manufacture
1. In the main vessel add water and cetrimonium chloride. Heat to 70-75° C.
2. In a separate vessel heat cetyl alcohol to 70-75° C.
3. Add the oil phase to the water phase and homogenise for 1 minute.
4. Cool to room temperature.
5. Stir in phenoxyethanol.
6. Dissolve ginkgo extract in glycerin and stir into bulk.
7. Dissolve emblica extract in 2% water and stir into bulk.
8. Dissolve dimethylmethoxy chromanol in alcohol denat. and stir into bulk.
9. Make to weight with water and stir smooth.

Example 9

Hair Conditioner

| Material | % w/w |
| --- | --- |
| Cetyl alcohol | 4 |
| Cetrimonium chloride | 3 |
| Phenoxyethanol | 0.6 |
| Glycerin | 2 |
| Alcohol denat. | 0.5 |
| Ginkgo extract | 0.01 |
| Emblica extract | 0.015 |
| Dimethylmethoxy chromanol | 0.02 |
| Aqua | To 100 |

Method of Manufacture
1. In the main vessel add water and cetrimonium chloride. Heat to 70-75° C.
2. In a separate vessel heat cetyl alcohol to 70-75° C.
3. Add the oil phase to the water phase and homogenise for 1 minute.
4. Cool to room temperature.
5. Stir in phenoxyethanol.
6. Dissolve ginkgo extract in glycerin and stir into bulk.
7. Dissolve emblica extract in 2% water and stir into bulk.
8. Dissolve dimethylmethoxy chromanol in alcohol denat. and stir into bulk.
9. Make to weight with water and stir smooth.

Example 10

Body Wash

| Material | % w/w |
| --- | --- |
| Sodium laureth sulphate | 36 |
| Cocamidopropyl betaine | 4 |
| Cocamide DEA | 1.5 |
| Sodium chloride | 1.5 |
| Sodium benzoate | 0.3 |
| Sodium methylparaben | 0.2 |
| Tetrasodium EDTA | 0.05 |
| Citric acid | 0.05 |
| Sodium hydroxide | 0.05 |
| Glycerin | 2 |
| Alcohol denat. | 0.5 |
| Ginkgo extract | 0.018 |
| Emblica extract | 0.013 |
| Rosemary extract | 0.001 |
| Aqua | To 100 |

Method of Manufacture
1. To water add and dissolve citric acid, sodium hydroxide, sodium chloride, sodium benzoate, sodium methylparaben and tetrasodium EDTA.
2. Stir in sodium laureth sulphate.
3. Stir in cocamide DEA.
4. Stir in cocamidopropyl betaine.
5. Dissolve ginkgo extract in glycerin and stir into bulk.
6. Dissolve emblica extract in 2% water and stir into bulk.
7. Dissolve rosemary extract in alcohol denat. and stir into bulk.
8. Make to weight with water and stir until uniform.

Example 11

Body Wash

| Material | % w/w |
| --- | --- |
| Sodium laureth sulphate | 36 |
| Cocamidopropyl betaine | 4 |
| Cocamide DEA | 1.5 |
| Sodium chloride | 1.5 |
| Sodium benzoate | 0.3 |
| Sodium methylparaben | 0.2 |
| Tetrasodium EDTA | 0.05 |
| Citric acid | 0.05 |
| Sodium hydroxide | 0.05 |
| Glycerin | 2 |
| Alcohol denat. | 0.5 |
| Potassium hydroxide | 0.015 |
| Ginkgo extract | 0.018 |
| Emblica extract | 0.013 |
| Dimethylmethoxy chromanol | 0.0018 |
| Ascorbyl glucoside | 0.05 |
| Aqua | To 100 |

Method of Manufacture

1. To water add and dissolve citric acid, sodium hydroxide, sodium chloride, sodium benzoate, sodium methylparaben and tetrasodium EDTA.
2. Stir in sodium laureth sulphate.
3. Stir in cocamide DEA.
4. Stir in cocamidopropyl betaine.
5. Dissolve ascorbyl glucoside in 2% water, neutralise with potassium hydroxide and stir into bulk.
6. Dissolve ginkgo extract in glycerin and stir into bulk.
7. Dissolve emblica extract in 2% water and stir into bulk.
8. Dissolve dimethylmethoxy chromanol in alcohol denat. and stir into bulk.
9. Make to weight with water and stir until uniform.

Example 12

Styling Spray

| Material | % w/w |
| --- | --- |
| Alcohol denat. | 70 |
| VP/VA copolymer | 5 |
| Polyquaternium 11 | 0.3 |
| Dimethylmethoxy chromanol | 0.0018 |
| Pine bark extract | 0.0017 |
| Rosemary extract | 0.0010 |
| Aqua | To 100 |

Method of Manufacture

1. To water add VPNA copolymer and polyquatemium 11. Stir until uniform (10 minutes)
2. In a separate vessel add alcohol denat., dimethylmethoxy chromanol, pine bark extract and rosemary extract. Stir until dissolved. Add this to the water phase and stir for 10 minutes until uniform.

Example 13

Styling Spray

| Material | % w/w |
| --- | --- |
| Alcohol denat. | 70 |
| VP/VA copolymer | 5 |
| Polyquaternium 11 | 0.3 |
| Emblica extract | 0.013 |
| Dimethylmethoxy chromanol | 0.0018 |
| Pine bark extract | 0.0017 |
| Aqua | To 100 |

Method of Manufacture

1. To water add emblica extract, VPNA copolymer and polyquaternium 11. Stir until uniform (10 minutes).
2. In a separate vessel add alcohol denat., dimethylmethoxy chromanol and pine bark extract. Stir until dissolved. Add this to the water phase and stir for 10 minutes until uniform.

Example 14

Lipstick

| Material | % w/w |
| --- | --- |
| Ricinus communis oil | 20 |
| Phenyl trimethicone | 15 |
| Polyethylene | 10 |
| C10-30 Cholesterol/lanesterol esters | 10 |
| Octyldodecanol | 10 |
| Hydrogenated polyisobutene | 8 |
| Cera microcrystallina | 7 |
| Mica | 5 |
| Pigment | 5 |
| Pearl | 10 |
| Glycerin | 1 |
| Alcohol denat. | 0.5 |
| Ginkgo extract | 0.018 |
| Emblica extract | 0.013 |
| Dimethylmethoxy chromanol | 0.0018 |

Method of Manufacture:

1. Disperse mica and pigment in *Ricinus ommunis* oil using an homogeniser until uniform.
2. Add phenyl trimethicone, polyethylene, C10-30 cholesterol/lanesterol esters, octyldodecanol, hydrogenated polyisobutene, Cera microcrystallina.
3. Heat to 80-85° C.
4. Stir in pearl.
5. Cool to 65° C.
6. Dissolve ginkgo extract in glycerin and stir into bulk.
7. Dissolve emblica extract in 1% water and stir into bulk
8. Dissolve dimethylmethoxy chromanol in alcohol denat. and stir into bulk.
9. Mould to desired shape and cool.

Example 15

Mousse

| Material | % w/w |
| --- | --- |
| Cyclopentasiloxane | 72.9955 |
| Mica | 11 |
| Dimethicone crosspolymer | 7.5 |
| Dimethicone copolyol | 2.5 |
| Pigment | 4 |
| Alcohol denat. | 1 |
| Aqua | 1 |
| Dimethylmethoxy chromanol | 0.0018 |
| Pine bark extract | 0.0017 |
| Rosemary extract | 0.0010 |

Method of Manufacture

1. Mix together cyclopentasiloxane and dimethicone copolyol.
2. Stir in mica and pigment until mixed and uniform (10 minutes).
3. Dissolve dimethylmethoxy chromanol, pine bark extract and rosemary extract in alcohol denat. Add aqua and stir into bulk.
4. Stir in dimethicone crosspolymer.

Example 16

Water-in-silicone Foundation Emulsion with SPF

| Material | % w/w |
| --- | --- |
| Aqua | To 100 |
| Cyclopentasiloxane | 20 |
| Ethylhexyl methoxycinnamate | 5 |
| Talc | 4 |
| Ethylhexyl stearate | 3 |
| Mica | 3 |
| Cyclohexasiloxane | 3 |
| Dimethicone crosspolymer | 3 |
| Dimethicone | 2.5 |
| Silica | 2 |
| Titanium dioxide | 2 |
| Butylene glycol | 2 |
| Disteardimonium hectorite | 1.5 |
| Dimethicone copolyol | 1.2 |
| Magnesium sulfate | 1 |
| Phenoxyethanol | 0.6 |
| Cetyl PEG/PPG-10/1 dimethicone | 0.5 |
| Hexyl Laurate | 0.5 |
| Polyglyceryl-4 isostearte | 0.5 |
| Propylene carbonate | 0.3 |
| Stearic acid | 0.15 |
| Triethoxycaprylylsilane | 0.13 |
| Methyl paraben | 0.13 |
| Butyl paraben | 0.03 |
| Ethyl paraben | 0.03 |
| Tetrasodium EDTA | 0.02 |
| Propyl paraben | 0.02 |
| Pigment | 10 |
| Ascorbyl glucoside | 0.05 |
| Potassium hydroxide | 0.015 |
| Alcohol denat. | 1 |
| Dimethylmethoxy chromanol | 0.0018 |
| Pine bark extract | 0.0017 |
| Rosemary extract | 0.0010 |
| White lupin peptides | 1 |
| Palmitoyl oligopeptide and Palmitoyl tetrapeptides | 1.5 |
| Retinyl palmitate | 0.07 |

Method of Manufacture
1. In the main vessel add cyclopentasiloxane, ethylhexyl methoxycinnamate, ethylhexyl stearate, cyclohexasiloxane, dimethicone, dimethicone copolyol, phenoxyethanol, cetyl PEG/PPG-10/1 dimethicone, hexyl laurate, polyglyceryl-4 isostearate, retinyl palmitate, methylparaben, butylparaben, ethylparaben, propylparaben. Heat to 40° C.
2. Disperse talc, mica, silica, titanium dioxide, stearic acid, triethoxycaprylsilane and pigment in the oil phase using an homogeniser until uniform (15 minutes).
3. Silverson in disteardimonium hectorite and propylene carbonate until uniform (5 minutes).
4. In a separate vessel weigh out water, butylene glycol, magnesium sulfate and tetrasodium EDTA. Stir until solids dissolve and heat to 40° C.
5. With both phases at 40° C. add the water phase slowly to the oil phase with stirring at high speed.
6. Cool below 35° C.
7. Dissolve ascorbyl glucoside in 2% water, neutralise with potassium hydroxide and stir into bulk.
8. Dissolve dimethylmethoxy chromanol, pine bark extract, rosemary extract in alcohol denat. Stir in 1% water and stir into bulk.
9. Stir in white lupin peptides, palmitoyl oligopeptide and palmitoyl tetrapeptide.
10. Homogenise for 5 minutes at 3500 rpm.
11. Stir in dimethicone crosspolymer and homogenise until smooth (2 minutes)

Example 17

Water-in-silicone Foundation Emulsion with SPF

| Material | % w/w |
| --- | --- |
| Aqua | To 100 |
| Cyclopentasiloxane | 20 |
| Ethylhexyl methoxycinnamate | 5 |
| Talc | 4 |
| Ethylhexyl stearate | 3 |
| Mica | 3 |
| Cyclohexasiloxane | 3 |
| Dimethicone crosspolymer | 3 |
| Dimethicone | 2.5 |
| Silica | 2 |
| Titanium dioxide | 2 |
| Butylene glycol | 2 |
| Disteardimonium hectorite | 1.5 |
| Dimethicone copolyol | 1.2 |
| Magnesium sulfate | 1 |
| Phenoxyethanol | 0.6 |
| Cetyl PEG/PPG-10/1 dimethicone | 0.5 |
| Hexyl Laurate | 0.5 |
| Polyglyceryl-4 isostearte | 0.5 |
| Propylene carbonate | 0.3 |
| Stearic acid | 0.15 |
| Triethoxycaprylylsilane | 0.13 |
| Methyl paraben | 0.13 |
| Butyl paraben | 0.03 |
| Ethyl paraben | 0.03 |
| Tetrasodium EDTA | 0.02 |
| Propyl paraben | 0.02 |
| Pigment | 10 |
| Ascorbyl glucoside | 0.05 |
| Potassium hydroxide | 0.015 |
| Alcohol denat. | 1 |
| Emblica extract | 0.013 |
| Dimethylmethoxy chromanol | 0.0018 |
| Rosemary extract | 0.001 |
| White lupin peptides | 1 |
| Palmitoyl oligopeptide and Palmitoyl tetrapeptides | 1.5 |
| Retinyl palmitate | 0.07 |

Method of Manufacture
1. In the main vessel add cyclopentasiloxane, ethylhexyl methoxycinnamate, ethylhexyl stearate, cyclohexasiloxane, dimethicone, dimethicone copolyol, phenoxyethanol, cetyl PEG/PPG-10/1 dimethicone, hexyl laurate, polyglyceryl-4 isostearate, retinyl palmitate, methylparaben, butylparaben, ethylparaben, propylparaben. Heat to 40° C.
2. Disperse talc, mica, silica, titanium dioxide, stearic acid, triethoxycaprylsilane and pigment in the oil phase using an homogeniser until uniform (15 minutes).
3. Silverson in disteardimonium hectorite and propylene carbonate until uniform (5 minutes).
4. In a separate vessel weigh out water, butylene glycol, magnesium sulfate and tetrasodium EDTA. Stir until solids dissolve and heat to 40° C.
5. With both phases at 40° C. add the water phase slowly to the oil phase with stirring at high speed.
6. Cool below 35° C.
7. Dissolve ascorbyl glucoside in 2% water, neutralise with potassium hydroxide and stir into bulk.
8. Dissolve dimethylmethoxy chromanol, and rosemary extract in alcohol denat. Stir in 1% water and stir into bulk.
9. Dissolve emblica extract in 2% water and stir into bulk.

10. Stir in white lupin peptides, palmitoyl oligopeptide and palmitoyl tetrapeptide.
11. Homogenise for 5 minutes at 3500 rpm.
12. Stir in dimethicone crosspolymer and homogenise until smooth (2 minutes)

Example 18

Water-in-Silicone Foundation Emulsion with SPF

| Material | % w/w |
|---|---|
| Aqua | To 100 |
| Cyclopentasiloxane | 20 |
| Ethylhexyl methoxycinnamate | 5 |
| Talc | 4 |
| Ethylhexyl stearate | 3 |
| Mica | 3 |
| Cyclohexasiloxane | 3 |
| Dimethicone crosspolymer | 3 |
| Dimethicone | 2.5 |
| Silica | 2 |
| Titanium dioxide | 2 |
| Butylene glycol | 2 |
| Disteardimonium hectorite | 1.5 |
| Dimethicone copolyol | 1.2 |
| Magnesium sulfate | 1 |
| Phenoxyethanol | 0.6 |
| Cetyl PEG/PPG-10/1 dimethicone | 0.5 |
| Hexyl Laurate | 0.5 |
| Polyglyceryl-4 isostearte | 0.5 |
| Propylene carbonate | 0.3 |
| Stearic acid | 0.15 |
| Triethoxycaprylylsilane | 0.13 |
| Methyl paraben | 0.13 |
| Butyl paraben | 0.03 |
| Ethyl paraben | 0.03 |
| Tetrasodium EDTA | 0.02 |
| Propyl paraben | 0.02 |
| Glycerin | 2 |
| Pigment | 10 |
| Ascorbyl glucoside | 0.05 |
| Potassium hydroxide | 0.015 |
| Alcohol denat. | 0.5 |
| Ginkgo extract | 0.01 |
| Emblica extract | 0.015 |
| Dimethylmethoxy chromanol | 0.02 |
| White lupin peptides | 1 |
| Palmitoyl oligopeptide and Palmitoyl tetrapeptides | 1.5 |
| Retinyl palmitate | 0.07 |

Method of Manufacture
1. In the main vessel add cyclopentasiloxane, ethylhexyl methoxycinnamate, ethylhexyl stearate, cyclohexasiloxane, dimethicone, dimethicone copolyol, phenoxyethanol, cetyl PEG/PPG-10/1 dimethicone, hexyl laurate, polyglyceryl-4 isostearate, retinyl palmitate, methylparaben, butylparaben, ethylparaben, propylparaben. Heat to 40° C.
2. Disperse talc, mica, silica, titanium dioxide, stearic acid, triethoxycaprylsilane and pigment in the oil phase using an homogeniser until uniform (15 minutes).
3. Silverson in disteardimonium hectorite and propylene carbonate until uniform (5 minutes).
4. In a separate vessel weigh out water, butylene glycol, magnesium sulfate and tetrasodium EDTA. Stir until solids dissolve and heat to 40° C.
5. With both phases at 40° C. add the water phase slowly to the oil phase with stirring at high speed.
6. Cool below 35° C.
7. Dissolve ascorbyl glucoside in 2% water, neutralise with potassium hydroxide and stir into bulk.
8. Dissolve ginkgo extract in glycerin and stir into bulk.
9. Dissolve dimethylmethoxy chromanol in alcohol denat.
10. Dissolve emblica extract in 2% water and stir into bulk.
11. Stir in white lupin peptides, palmitoyl oligopeptide and palmitoyl tetrapeptide.
12. Homogenise for 5 minutes at 3500 rpm.
13. Stir in dimethicone crosspolymer and homogenise until smooth (2 minutes).

Example 19

Oil-in-Water Foundation Emulsion with SPF

| Material | % w/w |
|---|---|
| Aqua | To 100 |
| Butylene dlycol | 6 |
| C12-15 alkyl benzoate | 5 |
| Ethylhexyl methoxycinnamate | 5 |
| Cyclopentasiloxane | 3.6 |
| Dimethicone | 3.5 |
| Steareth-21 | 3 |
| Cetyl Alcohol | 2 |
| Cyclohexasiloxane | 2 |
| Titanium dioxide | 2 |
| Steareth-2 | 1.5 |
| Mica | 1.2 |
| Kaolin | 1 |
| Phenoxyethanol | 0.8 |
| Sodium polyacrylate | 0.3 |
| Xanthan gum | 0.25 |
| Methyl paraben | 0.25 |
| Propylparaben | 0.15 |
| Pigment | 14 |
| Ascorbyl glucoside | 0.05 |
| Potassium hydroxide | 0.015 |
| Alcohol denat | 1 |
| Emblica extract | 0.013 |
| Dimethylmethoxy chromanol | 0.0018 |
| Pine bark extract | 0.0017 |
| White lupin peptides | 1 |
| Palmitoyl oligopeptide and Palmitoyl tetrapeptides | 1.5 |
| Retinyl palmitate | 0.07 |

Method of Manufacture
1. In the main vessel add water, butylene glycol, sodium polyacrylate.
2. Homogenise in titanium dioxide, mica, kaolin and pigment until uniform.
3. Homogenise in xanthan gum until uniform. Heat to 70-75° C.
4. In a separate vessel add C12-15 alkyl benzoate, ethylhexyl methoxycinnamate, cyclopentasiloxane, dimethicone, steareth-21, cetyl alcohol, cyclohexasiloxane, steareth-2, retinyl palmitate, phenoxyethanol, methylparaben and propylparaben. Heat to 70-75° C.
5. Add the oil phase to the water phase and homogenise for 5 minutes.
6. Cool below 35° C.
7. Dissolve ascorbyl glucoside in 2% water, neutralise with potassium hydroxide and stir into bulk.
8. Dissolve emblica extract in 2% water and stir into bulk.
9. Dissolve dimethylmethoxy chromanol and pine bark extract in alcohol denat. Stir in 1% aqua and stir into bulk.
10. Stir in white lupin peptides, palmitoyl oligopeptide and palmitoyl tetrapeptides.
11. Make to weight and stir until smooth.

Example 20

Oil-in-Water Foundation Emulsion with SPF

| Material | % w/w |
|---|---|
| Aqua | To 100 |
| Butylene dlycol | 6 |
| C12-15 alkyl benzoate | 5 |
| Ethylhexyl methoxycinnamate | 5 |
| Cyclopentasiloxane | 3.6 |
| Dimethicone | 3.5 |
| Steareth-21 | 3 |
| Cetyl Alcohol | 2 |
| Cyclohexasiloxane | 2 |
| Titanium dioxide | 2 |
| Steareth-2 | 1.5 |
| Mica | 1.2 |
| Kaolin | 1 |
| Phenoxyethanol | 0.8 |
| Sodium polyacrylate | 0.3 |
| Xanthan gum | 0.25 |
| Methyl paraben | 0.25 |
| Propylparaben | 0.15 |
| Pigment | 14 |
| Ascorbyl glucoside | 0.05 |
| Potassium hydroxide | 0.015 |
| Alcohol denat. | 0.5 |
| Glycerin | 2 |
| Ginkgo extract | 0.005 |
| Emblica extract | 0.015 |
| Dimethylmethoxy chromanol | 0.02 |
| White lupin peptides | 1 |
| Palmitoyl oligopeptide and Palmitoyl tetrapeptides | 1.5 |
| Retinyl palmitate | 0.07 |

Method of Manufacture

1. In the main vessel add 48% water, butylene glycol, sodium polyacrylate.
2. Homogenise in titanium dioxide, mica, kaolin and pigment until uniform.
3. Homogenise in xanthan gum until uniform. Heat to 70-75° C.
4. In a separate vessel add C12-15 alkyl benzoate, ethylhexyl methoxycinnamate, cyclopentasiloxane, dimethicone, steareth-21, cetyl alcohol, cyclohexasiloxane, steareth-2, retinyl palmitate, phenoxyethanol, methylparaben and propylparaben. Heat to 70-75° C.
5. Add the oil phase to the water phase and homogenise for 5 minutes.
6. Cool below 35° C.
7. Dissolve ascorbyl glucoside in 2% water, neutralise with potassium hydroxide and stir into bulk.
8. Dissolve emblica extract in 2% water and stir into bulk.
9. Dissolve dimethylmethoxy chromanol in alcohol denat. stir into bulk.
10. Dissolve ginkgo extract in glycerin and stir into bulk.
11. Stir in white lupin peptides, palmitoyl oligopeptide and palmitoyl tetrapeptides.
12. Make to weight and stir until smooth.

Example 21

Eye Cream

| Material | % w/w |
|---|---|
| Aqua | To 100 |
| Caprylic/capric triglyceride | 5 |
| Glycerin | 3 |
| Petrolatum | 3 |
| Helianthus annuus seed oil | 3 |
| Cetearyl alcohol | 2.4 |
| Paraffin | 2 |
| Dimethicone | 1 |
| Glyceryl stearate | 1 |
| Cetyl alcohol | 1 |
| Phenoxyethanol | 0.6 |
| PEG-20 stearate | 0.6 |
| Methylparaben | 0.25 |
| Ethylparaben | 0.1 |
| Carbomer | 0.2 |
| Potassium hydroxide | 0.07 |
| Tetrasodium EDTA | 0.02 |
| Ascorbyl glucoside | 0.05 |
| Potassium hydroxide | 0.015 |
| Alcohol denat. | 0.5 |
| Ginkgo extract | 0.0018 |
| Emblica extract | 0.013 |
| Dimethylmethoxy chromanol | 0.018 |
| White lupin peptides | 1 |
| Palmitoyl oligopeptide and Palmitoyl tetrapeptides | 1.5 |
| Retinyl palmitate | 0.07 |

Method of Manufacture

1. In the main vessel add water, add and dissolve tetrasodium EDTA.
2. With homogenisation sprinkle in carbomer. Continue to homogensie for 5 minutes. Add methylparaben and ethylparaben and heat to 70-75° C.
3. In a separate vessel add caprylic/capric triglyceride, petrolatum, *helianthus annuus* seed oil, cetearyl alcohol, paraffin, dimethicone, glyceryl stearate, cetyl alcohol, retinyl palmitate, phenoxyethanol and PEG-20 stearate. Heat to 70-75° C.
4. With both phases at 70-75° C. add the oil phase to the water phase and homogenise for 2 minutes.
5. Add potassium hydroxide and homogenise for 2 minutes.
6. Cool below 35° C.
7. Dissolve ascorbyl glucoside in 2% water, neutralise with potassium hydroxide and stir into bulk.
8. Dissolve ginkgo extract in glycerin and stir into bulk.
9. Dissolve emblica in 2% water and stir into bulk.
10. Dissolve dimethylmethoxy chromanol in alcohol denat. and stir into bulk.
11. Stir in white lupin peptides, palmitoyl oligopeptide and palmitoyl tetrapeprides.
12. Make to weight and stir smooth.

Example 22

Eye Cream

| Material | % w/w |
|---|---|
| Aqua | To 100 |
| Caprylic/capric triglyceride | 5 |
| Glycerin | 3 |

| Material | % w/w |
| --- | --- |
| Petrolatum | 3 |
| Helianthus annuus seed oil | 3 |
| Cetearyl alcohol | 2.4 |
| Paraffin | 2 |
| Dimethicone | 1 |
| Glyceryl stearate | 1 |
| Cetyl alcohol | 1 |
| Phenoxyethanol | 0.6 |
| PEG-20 stearate | 0.6 |
| Methylparaben | 0.25 |
| Ethylparaben | 0.1 |
| Carbomer | 0.2 |
| Potassium hydroxide | 0.07 |
| Tetrasodium EDTA | 0.02 |
| Ascorbyl glucoside | 0.05 |
| Potassium hydroxide | 0.015 |
| Alcohol denat. | 0.5 |
| Ginkgo extract | 0.005 |
| Emblica extract | 0.015 |
| Dimethylmethoxy chromanol | 0.02 |
| White lupin peptides | 1 |
| Palmitoyl oligopeptide and Palmitoyl tetrapeptides | 1.5 |
| Retinyl palmitate | 0.07 |

Method of Manufacture
1. In the main vessel add water, add and dissolve tetrasodium EDTA.
2. With homogenisation sprinkle in carbomer. Continue to homogensie for 5 minutes. Add methylparaben and ethylparaben and heat to 70-75° C.
3. In a separate vessel add caprylic/capric triglyceride, petrolatum, *helianthus annuus* seed oil, cetearyl alcohol, paraffin, dimethicone, glyceryl stearate, cetyl alcohol, retinyl palmitate, phenoxyethanol and PEG-20 stearate. Heat to 70-75° C.
4. With both phases at 70-75° C. add the oil phase to the water phase and homogenise for 2 minutes.
5. Add potassium hydroxide and homogenise for 2 minutes.
6. Cool below 35° C.
7. Dissolve ascorbyl glucoside in 2% water, neutralise with potassium hydroxide and stir into bulk.
8. Dissolve ginkgo extract in glycerin and stir into bulk.
9. Dissolve emblica in 2% water and stir into bulk.
10. Dissolve dimethylmethoxy chromanol in alcohol denat. and stir into bulk.
11. Stir in white lupin peptides, palmitoyl oligopeptide and palmitoyl tetrapeprides.
12. Make to weight and stir smooth.

Example 23

Body Lotion

| Material | % w/w |
| --- | --- |
| Aqua | To 100 |
| Paraffin liquidum | 20 |
| Hydrogenated vegetable glycerides citrate | 1 |
| Phenoxyethanol | 0.6 |
| Carbomer | 0.32 |
| Methylparaben | 0.2 |
| Tetrasodium EDTA | 0.05 |
| Potassium hydroxide | 0.09 |
| Ethylparaben | 0.1 |
| Ascorbyl glucoside | 0.05 |
| Potassium hydroxide | 0.015 |
| Alcohol denat. | 1 |
| Dimethylmethoxy chromanol | 0.0018 |
| Pine bark extract | 0.0017 |
| Rosemary extract | 0.0010 |
| White lupin peptides | 1 |
| Palmitoyl oligopeptide and Palmitoyl tetrapeptides | 1.5 |
| Retinyl palmitate | 0.07 |

Method of Manufacture
1. In the main vessel add water, add and dissolve tetrasodium EDTA.
2. With homogenisation sprinkle in carbomer and homogenise for 2 minutes. Add methylparaben and ethylparaben and heat to 70-75° C.
3. In a separate vessel add paraffin liquidum, hydrogenated vegetable glycerides citrate, retinyl palmitate and phenoxyethanol. Heat to 70-75° C.
4. With both phases at 70-75° C. add the oil phase to the water phase and homogenise for 2 minutes. Add potassium hydroxide and homogenise for 2 minutes.
5. Cool below 35° C.
6. Dissolve ascorbyl glucoside in 2% water, neutralise with potassium hydroxide and stir into bulk.
7. Dissolve dimethylmethoxy chromanol, pine bark extract and rosemary extract in alcohol denat. Stir in 1% water and stir into bulk.
8. Stir in white lupin peptides, palmitoyl oligopeptide and palmitoyl tetrapeptides.
9. Make to weight and stir smooth.

Example 24

Body Lotion

| Material | % w/w |
| --- | --- |
| Aqua | To 100 |
| Paraffin liquidum | 20 |
| Hydrogenated vegetable glycerides citrate | 1 |
| Phenoxyethanol | 0.6 |
| Carbomer | 0.32 |
| Methylparaben | 0.2 |
| Tetrasodium EDTA | 0.05 |
| Potassium hydroxide | 0.09 |
| Ethylparaben | 0.1 |
| Ascorbyl glucoside | 0.05 |
| Potassium hydroxide | 0.015 |
| Alcohol denat. | 1 |
| Emblica extract | 0.013 |
| Dimethylmethoxy chromanol | 0.0018 |
| Rosemary extract | 0.001 |
| White lupin peptides | 1 |
| Palmitoyl oligopeptide and Palmitoyl tetrapeptides | 1.5 |
| Retinyl palmitate | 0.07 |

Method of Manufacture
1. In the main vessel add water, add and dissolve tetrasodium EDTA.
2. With homogenisation sprinkle in carbomer and homogenise for 2 minutes. Add methylparaben and ethylparaben and heat to 70-75° C.

3. In a separate vessel add paraffin liquidum, hydrogenated vegetable glycerides citrate, retinyl palmitate and phenoxyethanol. Heat to 70-75° C.
4. With both phases at 70-75° C. add the oil phase to the water phase and homogenise for 2 minutes. Add potassium hydroxide and homogenise for 2 minutes.
5. Cool below 35° C.
6. Dissolve ascorbyl glucoside in 2% water, neutralise with potassium hydroxide and stir into bulk.
7. Dissolve emblica in 2% water and stir into bulk.
8. Dissolve dimethylmethoxy chromanol and rosemary extract in alcohol denat. Stir in 1% water and stir into bulk.
9. Stir in white lupin peptides, palmitoyl oligopeptide and palmitoyl tetrapeptides.
10. Make to weight and stir smooth.

Example 25

Skin Cream

| Material | % w/w |
| --- | --- |
| Paraffinum liquidum | 10 |
| Cetearyl alcohol | 2 |
| Glycerin | 2 |
| Glyceryl stearate | 2 |
| Cetyl alcohol | 2 |
| PEG-100 stearate | 2 |
| Dimethicone | 1.5 |
| PEG-20 stearate | 0.5 |
| Phenoxyethanol | 0.4 |
| Carbomer | 0.2 |
| Methylparaben | 0.2 |
| Propylparaben | 0.15 |
| Potassium hydroxide | 0.06 |
| Potassium hydroxide | 0.015 |
| Alcohol denat. | 0.5 |
| Tetrasodium EDTA | 0.05 |
| Ascorbyl glucoside | 0.05 |
| Ginkgo extract | 0.005 |
| Emblica extract | 0.015 |
| Pine Bark Extract | 0.0017 |
| White lupin peptides | 1 |
| Palmitoyl oligopeptide and Palmitoyl tetrapeptides | 1.5 |
| Retinyl palmitate | 0.07 |
| Aqua | To 100 |

Method of Manufacture
1. To water add and dissolve tetrasodium EDTA.
2. Using homogenisation sprinkle in carbomer and continue to homogenise for 5 minutes or until hydrated.
3. Add methylparaben and heat up to 70-75° C.
4. In a separate vessel weigh out oil phase and heat to 70-75° C. (Paraffin liquidum, cetearyl alcohol, glyceryl stearate, cetyl alcohol, PEG-100 stearate, dimethicone, PEG-20 stearate, phenoxyethanol, retinyl palmitate and propylparaben.)
5. With both phases at 70-75° C. add the oil phase to the water phase and homogenise for 2 minutes.
6. Add potassium hydroxide and homogenise for 2 minutes.
21. Cool to room temperature.
22. Dissolve ascorbyl glucoside in 2% water, neutralise with potassium hydroxide and stir into bulk.
23. Dissolve ginkgo extract in glycerin and stir into bulk.
24. Dissolve emblica extract in 2% water and stir into bulk.
25. Dissolve Pine bark extract in alcohol denat. and stir into bulk.
26. Stir into bulk white lupin peptides, palmitoyl oligopeptide and palmitoyl tetrapeptides
27. Make to weight with water and stir smooth.

Example 26

Water-in-Silicone Foundation Emulsion with SPF

| Material | % w/w |
| --- | --- |
| Aqua | To 100 |
| Cyclopentasiloxane | 20 |
| Ethylhexyl methoxycinnamate | 5 |
| Talc | 4 |
| Ethylhexyl stearate | 3 |
| Mica | 3 |
| Cyclohexasiloxane | 3 |
| Dimethicone crosspolymer | 3 |
| Dimethicone | 2.5 |
| Silica | 2 |
| Titanium dioxide | 2 |
| Butylene glycol | 2 |
| Disteardimonium hectorite | 1.5 |
| Dimethicone copolyol | 1.2 |
| Magnesium sulfate | 1 |
| Phenoxyethanol | 0.6 |
| Cetyl PEG/PPG-10/1 dimethicone | 0.5 |
| Hexyl Laurate | 0.5 |
| Polyglyceryl-4 isostearte | 0.5 |
| Propylene carbonate | 0.3 |
| Stearic acid | 0.15 |
| Triethoxycaprylylsilane | 0.13 |
| Methyl paraben | 0.13 |
| Butyl paraben | 0.03 |
| Ethyl paraben | 0.03 |
| Tetrasodium EDTA | 0.02 |
| Propyl paraben | 0.02 |
| Pigment | 10 |
| Ascorbyl glucoside | 0.05 |
| Potassium hydroxide | 0.015 |
| Alcohol denat. | 1 |
| Emblica extract | 0.015 |
| Pine bark extract | 0.0017 |
| Rosemary extract | 0.0010 |
| White lupin peptides | 1 |
| Palmitoyl oligopeptide and Palmitoyl tetrapeptides | 1.5 |
| Retinyl palmitate | 0.07 |

Method of Manufacture
1. In the main vessel add cyclopentasiloxane, ethylhexyl methoxycinnamate, ethylhexyl stearate, cyclohexasiloxane, dimethicone, dimethicone copolyol, phenoxyethanol, cetyl PEG/PPG-10/1 dimethicone, hexyl laurate, polyglyceryl-4 isostearate, retinyl palmitate, methylparaben, butylparaben, ethylparaben, propylparaben. Heat to 40° C.
2. Disperse talc, mica, silica, titanium dioxide, stearic acid, triethoxycaprylsilane and pigment in the oil phase using an homogeniser until uniform (15 minutes).
3. Silverson in disteardimonium hectorite and propylene carbonate until uniform (5 minutes).
4. In a separate vessel weigh out water, butylene glycol, magnesium sulfate and tetrasodium EDTA. Stir until solids dissolve and heat to 40° C.
5. With both phases at 40° C. add the water phase slowly to the oil phase with stirring at high speed.
12. Cool below 35° C.
13. Dissolve ascorbyl glucoside in 2% water, neutralise with potassium hydroxide and stir into bulk.
14. Dissolve pine bark extract, rosemary extract in alcohol denat. Stir in 1% water and stir into bulk.

15. Dissolve emblica extract in 2% water and stir into bulk.
16. Stir in white lupin peptides, palmitoyl oligopeptide and palmitoyl tetrapeptide.
17. Homogenise for 5 minutes at 3500 rpm.
18. Stir in dimethicone crosspolymer and homogenise until smooth (2 minutes)

Example 27

Skin Cream with SPF

| Material | % w/w |
|---|---|
| C12-15 alkyl benzoate | 5 |
| Butyl methoxydibenzoylmethane | 3 |
| Ethylhexyl methoxycinnamate | 5 |
| Cetearyl alcohol | 2 |
| Glycerin | 2 |
| Glyceryl stearate | 2 |
| Cetyl alcohol | 2 |
| PEG-100 stearate | 2 |
| Dimethicone | 1.5 |
| PEG-20 stearate | 0.5 |
| Phenoxyethanol | 0.4 |
| Carbomer | 0.2 |
| Methylparaben | 0.2 |
| Propylparaben | 0.15 |
| Potassium hydroxide | 0.06 |
| Potassium hydroxide | 0.015 |
| Alcohol denat. | 0.5 |
| Tetrasodium EDTA | 0.05 |
| Ascorbyl glucoside | 0.05 |
| Ginkgo extract | 0.005 |
| Pine bark extract | 0.0017 |
| Dimethylmethoxy chromanol | 0.02 |
| White lupin peptides | 1 |
| Palmitoyl oligopeptide and Palmitoyl tetrapeptides | 1.5 |
| Retinyl palmitate | 0.07 |
| Aqua | To 100 |

Method of Manufacture
1. To water add and dissolve tetrasodium EDTA.
2. Using homogenisation sprinkle in carbomer and continue to homogenise for 5 minutes or until hydrated.
3. Add methylparaben and heat up to 70-75° C.
4. In a separate vessel weigh out oil phase and heat to 70-75° C. (C12-15 alkyl benzoate, butyl methoxydibenzoylmethane, ethylhexyl methoxydibenzoylmethane, cetearyl alcohol, glyceryl stearate, cetyl alcohol, PEG-100 stearate, dimethicone, PEG-20 stearate, phenoxyethanol, retinyl palmitate and propylparaben)
5. With both phases at 70-75° C. add the oil phase to the water phase and homogenise for 2 minutes.
6. Add potassium hydroxide and homogenise for 2 minutes.
14. Cool to room temperature.
15. Dissolve ascorbyl glucoside in 2% water, neutralise with potassium hydroxide and stir into bulk.
16. Dissolve gingko extract in glycerin and stir into bulk.
17. Dissolve dimethylmethoxy chromanol and pine bark extract in alcohol denat. Stir in 1% water and stir into bulk.
18. Stir into bulk White lupin peptides, palmitoyl oligopeptide and palmitoyl tetrapeptides
19. Make to weight with water and stir smooth.

Example 28

Water-in-Oil Emulsion

| Material | % w/w |
|---|---|
| Paraffinum liquidum | 8 |
| Ethylhexyl stearate | 7 |
| Isopropyl myristate | 5 |
| Glycerin | 3 |
| Polyglyceryl-3 oleate | 1.7 |
| Butylene glycol | 1.4 |
| Cetyl PEG/PPG-10/1 dimethicone | 1.3 |
| Sodium chloride | 0.75 |
| Magnesium sulfate | 0.75 |
| Phenoxyethanol | 0.7 |
| Methylparaben | 0.2 |
| Ethylparaben | 0.1 |
| Ascorbyl glucoside | 0.05 |
| Potassium hydroxide | 0.015 |
| Ginkgo extract | 0.005 |
| Rosemary extract | 0.001 |
| Dimethylmethoxy chromanol | 0.02 |
| Alcohol denat. | 0.5 |
| White lupin peptides | 2 |
| Palmitoyl oligopeptide and Palmitoyl tetrapeptides | 3 |
| Retinyl palmitate | 0.07 |
| Aqua | To 100 |

Method of Manufacture
1. In the main vessel add paraffin liquidum, ethylhexyl stearate, isopropyl myristate, polyglyceryl-3 oleate, cetyl PEG/PPG-10/1 dimethicone and retinyl palmitate.
2. Separately weigh out water, sodium chloride, magnesium sulfate, butylene glycol.
3. Separately mix together phenoxyethanol, methylparaben and ethylparaben. Heat until dissolved and add to the water phase.
9. Add the water phase to the oil phase slowly with constant stirring at high speed. Continue stirring for 5 minutes.
10. Dissolve ascorbyl glucoside in 2% water, neutralise with potassium hydroxide and stir into bulk.
11. Dissolve gingko extract in glycerin and stir into bulk.
12. Dissolve dimethylmethoxy chromanol and rosemary extract in alcohol denat. Add 1% water and stir into bulk.
13. Stir into bulk white lupin peptides, palmitoyl oligopeptide and palmitoyl tetrapeptides.
14. Homogenise the product for 5 minutes at 3500 rpm.

Example 29

Antioxidant Testing for Combinations of Three Antioxidant Agents Selected from List A Method
1. The antioxidant agents (referred to as raw materials (RM) hereafter) were first dissolved in an appropriate solvent as detailed in Table 1.
2. Combinations of three raw materials were prepared for testing by combining one part each of three raw material dilutions, at the concentrations specified in Table 2.
3. In Table 2 each combination is given a combination number and each combination number is further described as A, B or C, where the concentrations of the raw material dilutions used in B are ten times greater that A, and the concentrations used in C are ten times greater than B (one hundred times greater than A).

4. The concentrations of raw materials provided in Table 2 are the final concentrations of those materials in the ABEL® antioxidant assay.

TABLE 1

Raw materials and solvents used

| RM name | RM number | Solvent |
|---|---|---|
| ginkgo extract | 2 | 1:1 IMS:water |
| emblica extract | 9 | water |
| dimethylmethoxy chromanol | 10 | IMS |
| pine bark extract | 15 | 1:1 IMS:water |
| rosemary extract | 19 | 1:1 IMS:water |

TABLE 2

Concentrations of raw materials used in each combination tested

All concentrations are mg/mL and are the final concentrations in the ABEL ® assay for peroxynitrite

| Combination Number | RM number | RM conc (%) | RM number | RM conc (%) | RM number | RM conc (%) |
|---|---|---|---|---|---|---|
| 1A | 10 | 0.00018 | 15 | 0.00017 | 19 | 0.0001 |
| 1B | 10 | 0.0018 | 15 | 0.0017 | 19 | 0.001 |
| 1C | 10 | 0.018 | 15 | 0.017 | 19 | 0.01 |
| 2A | 9 | 0.0013 | 15 | 0.00017 | 19 | 0.0001 |
| 2B | 9 | 0.013 | 15 | 0.0017 | 19 | 0.001 |
| 2C | 9 | 0.13 | 15 | 0.017 | 19 | 0.01 |
| 3A | 9 | 0.0013 | 10 | 0.00018 | 19 | 0.0001 |
| 3B | 9 | 0.013 | 10 | 0.0018 | 19 | 0.001 |
| 3C | 9 | 0.13 | 10 | 0.018 | 19 | 0.01 |
| 4A | 9 | 0.0013 | 10 | 0.00018 | 15 | 0.00017 |
| 4B | 9 | 0.013 | 10 | 0.0018 | 15 | 0.0017 |
| 4C | 9 | 0.13 | 10 | 0.018 | 15 | 0.017 |
| 5A | 2 | 0.0018 | 15 | 0.00017 | 19 | 0.0001 |
| 5B | 2 | 0.018 | 15 | 0.0017 | 19 | 0.001 |
| 5C | 2 | 0.18 | 15 | 0.017 | 19 | 0.01 |
| 6A | 2 | 0.0018 | 10 | 0.00018 | 15 | 0.00017 |
| 6B | 2 | 0.018 | 10 | 0.0018 | 15 | 0.0017 |
| 6C | 2 | 0.18 | 10 | 0.018 | 15 | 0.017 |
| 7A | 2 | 0.0018 | 9 | 0.0013 | 15 | 0.00017 |
| 7B | 2 | 0.018 | 9 | 0.013 | 15 | 0.0017 |
| 7C | 2 | 0.18 | 9 | 0.13 | 15 | 0.017 |
| 8A | 2 | 0.0018 | 9 | 0.0013 | 10 | 0.00018 |
| 8B | 2 | 0.018 | 9 | 0.013 | 10 | 0.0018 |
| 8C | 2 | 0.18 | 9 | 0.13 | 10 | 0.018 |
| 9A | 2 | 0.0018 | 9 | 0.0013 | 19 | 0.0001 |
| 9B | 2 | 0.018 | 9 | 0.013 | 19 | 0.001 |
| 9C | 2 | 0.18 | 9 | 0.13 | 19 | 0.01 |
| 10A | 2 | 0.0018 | 10 | 0.00018 | 19 | 0.0001 |
| 10B | 2 | 0.018 | 10 | 0.0018 | 19 | 0.001 |
| 10C | 2 | 0.18 | 10 | 0.018 | 19 | 0.01 |

FIGS. 1-10 show the results of the ABEL® antioxidant assay for peroxynitrite, for each of combinations 1-10.

Summary

Raw material combinations 1, 3, 4, 8 and 9 gave the best synergies or displayed a delay in the time to peak, and were therefore the combinations that were analysed further.

Example 30

Further Antioxidant Testing on Selected Combinations of Three Antioxidant Agents from List A Raw material combinations 1, 3, 4, 8 and 9 were assayed at three additional concentrations which are dilutions of concentration A (see Table 2). The details are contained in Table 3.

TABLE 3

Concentrations of raw materials used in each combination tested

All concentrations are mg/mL and are the final concentrations used in the ABEL ® assay for peroxynitrite

| Combination number | RM number | RM conc (%) | RM number | RM conc (%) | RM number | RM conc (%) |
|---|---|---|---|---|---|---|
| 1 | 10 | 0.00018 | 15 | 0.000170 | 19 | 0.00010 |
| 1 | 10 | 0.00009 | 15 | 0.000085 | 19 | 0.00005 |
| 1 | 10 | 0.000036 | 15 | 0.000034 | 19 | 0.00002 |
| 1 | 10 | 0.000018 | 15 | 0.000017 | 19 | 0.00001 |
| 3 | 9 | 0.0013 | 10 | 0.000180 | 19 | 0.00010 |
| 3 | 9 | 0.00065 | 10 | 0.000090 | 19 | 0.00005 |
| 3 | 9 | 0.00026 | 10 | 0.000036 | 19 | 0.00002 |
| 3 | 9 | 0.00013 | 10 | 0.000018 | 19 | 0.00001 |
| 4 | 9 | 0.0013 | 10 | 0.000180 | 15 | 0.00017 |
| 4 | 9 | 0.00065 | 10 | 0.000090 | 15 | 0.00009 |
| 4 | 9 | 0.00026 | 10 | 0.000036 | 15 | 0.00003 |
| 4 | 9 | 0.00013 | 10 | 0.000018 | 15 | 0.00002 |
| 8 | 2 | 0.0018 | 9 | 0.001300 | 10 | 0.00018 |
| 8 | 2 | 0.0009 | 9 | 0.000650 | 10 | 0.00180 |
| 8 | 2 | 0.00036 | 9 | 0.000260 | 10 | 0.01800 |
| 8 | 2 | 0.00018 | 9 | 0.000130 | 10 | 0.00002 |
| 9 | 2 | 0.0018 | 9 | 0.001300 | 19 | 0.00010 |
| 9 | 2 | 0.0009 | 9 | 0.000650 | 19 | 0.00005 |
| 9 | 2 | 0.00036 | 9 | 0.000260 | 19 | 0.00002 |
| 9 | 2 | 0.00018 | 9 | 0.000130 | 19 | 0.00001 |

FIGS. 11-15 show the results of the ABEL® antioxidant assay for peroxynitrite.

Example 31

Tables Showing ABEL-RAC Scores for Combinations of Three Raw Materials Compared to the Sum of the Abel-Rac Scores for Each Individual Raw Material, and Calculated Synergy Values

TABLE 4

Combination 1

| Ingredient | EC50 mg/mL of pure ingredient | ABEL-RAC peroxynitrite of pure ingredient | Percentage of ingredient in combination | ABEL-RAC contribution in combination |
|---|---|---|---|---|
| RM10 | 0.0018 | 88053 | 40 | 35221 |
| RM15 | 0.0017 | 106837 | 38 | 40361 |
| RM19 | 0.0010 | 799816 | 22 | 177737 |
| | SUM | | | 253319 |
| ABEL-RAC PEROXYNITRITE-COMBINATION 1 | | | | 396562 |
| | SYNERGY | | | 1.57 |

TABLE 5

Combination 3

| Ingredient | EC50 mg/mL of pure ingredient | ABEL-RAC peroxynitrite of pure ingredient | Percentage of ingredient in combination | ABEL-RAC contribution in combination |
|---|---|---|---|---|
| RM9 | 0.0130 | 78317 | 82 | 64438 |
| RM10 | 0.0018 | 88053 | 11 | 10031 |
| RM19 | 0.0010 | 759825 | 6 | 45590 |
| | SUM | | | 120059 |
| ABEL-RAC PEROXYNITRITE-COMBINATION 3 | | | | 119470 |
| | SYNERGY | | | 1.00 |

TABLE 6

Combination 4

| Ingredient | EC50 mg/mL of pure ingredient | ABEL-RAC peroxynitrite of pure ingredient | Percentage of ingredient in combination | ABEL-RAC contribution in combination |
|---|---|---|---|---|
| RM9 | 0.0130 | 78317 | 79 | 61704 |
| RM10 | 0.0018 | 88053 | 11 | 9606 |
| RM15 | 0.0017 | 101495 | 10 | 10457 |
| | | SUM | | 81767 |
| ABEL-RAC PEROXYNITRITE-COMBINATION 4 | | | | 111499 |
| | | SYNERGY | | 1.36 |

TABLE 7

Combination 8

| Ingredient | EC50 mg/mL of pure ingredient | ABEL-RAC peroxynitrite of pure ingredient | Percentage of ingredient in combination | ABEL-RAC contribution in combination |
|---|---|---|---|---|
| RM2 | 0.0180 | 72807 | 55 | 39955 |
| RM9 | 0.0130 | 78317 | 40 | 31327 |
| RM10 | 0.0018 | 88053 | 5 | 4832 |
| | | SUM | | 76114 |
| ABEL-RAC PEROXYNITRITE-COMBINATION 8 | | | | 111499 |
| | | SYNERGY | | 1.46 |

TABLE 8

Combination 9

| Ingredient | EC50 mg/mL of pure ingredient | ABEL-RAC peroxynitrite of pure ingredient | Percentage of ingredient in combination | ABEL-RAC contribution in combination |
|---|---|---|---|---|
| RM2 | 0.0180 | 72807 | 56 | 40954 |
| RM9 | 0.0130 | 78317 | 41 | 31816 |
| RM19 | 0.0010 | 759825 | 3 | 23745 |
| | | SUM | | 96515 |
| ABEL-RAC PEROXYNITRITE-COMBINATION 9 | | | | 125816 |
| | | SYNERGY | | 1.30 |

Example 32

Antioxidant Testing for Combinations of Three Antioxidant Agents Selected from List A in a Cream Base 1. The raw materials were diluted with solvent as detailed in Table 1, to concentrations one hundred times stronger that the target concentration in the cream. Table 9 shows the concentrations of the raw materials that were used for each of the three combinations tested.
2. 100 µL of each raw material (ie 300 µL in total) was added to 9.7 g of the base cream. (It was assumed that the density of the cream was equivalent to the density of water). The cream was stirred gently with a flat plastics stick ensuring homogeneity before making further dilutions. For the cream control, 300 µL solvent (without raw materials) was added to 9.7 g of the cream base.
3. The cream combinations and the cream control were diluted with assay buffer (PBS) in the same ratio to produce the following cream concentrations: 4 mg/mL, 10 mg/mL, 20 mg/mL and 100 mg/mL. Thus, the working concentration used was based on the cream concentration, and the ratio between base cream and raw material is kept constant.
4. In the antioxidant assay with peroxynitrite, 100 µL of diluted cream was added to a well of a microplate, the final volume of the assay being 200 µL.

TABLE 9

Concentrations of raw materials used in each cream combination

| Cream combination number | RM number | Target concentration in cream (%) | Stock concentration of RM in solvent mg/ml |
|---|---|---|---|
| 1 | 10 | 0.0018 | 18 |
| | 15 | 0.0017 | 17 |
| | 19 | 0.0010 | 10 |
| 8 | 2 | 0.018 | 180 |
| | 9 | 0.013 | 130 |
| | 10 | 0.0018 | 18 |
| 8 modified | 2 | 0.0018 | 18 |
| | 9 | 0.013 | 130 |
| | 10 | 0.018 | 180 |

Figure 16:
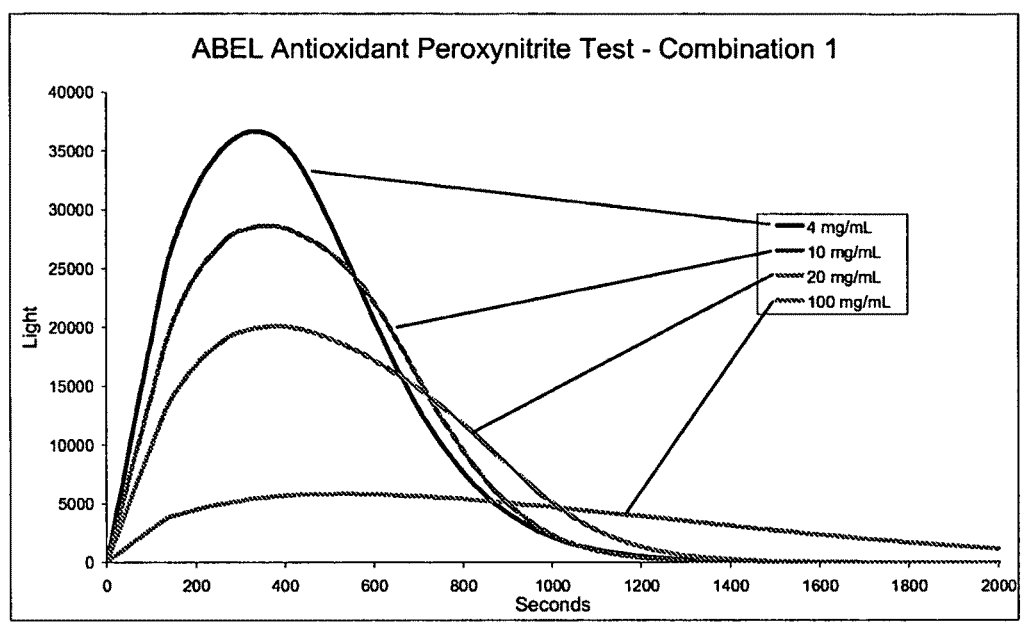
Figure 17:
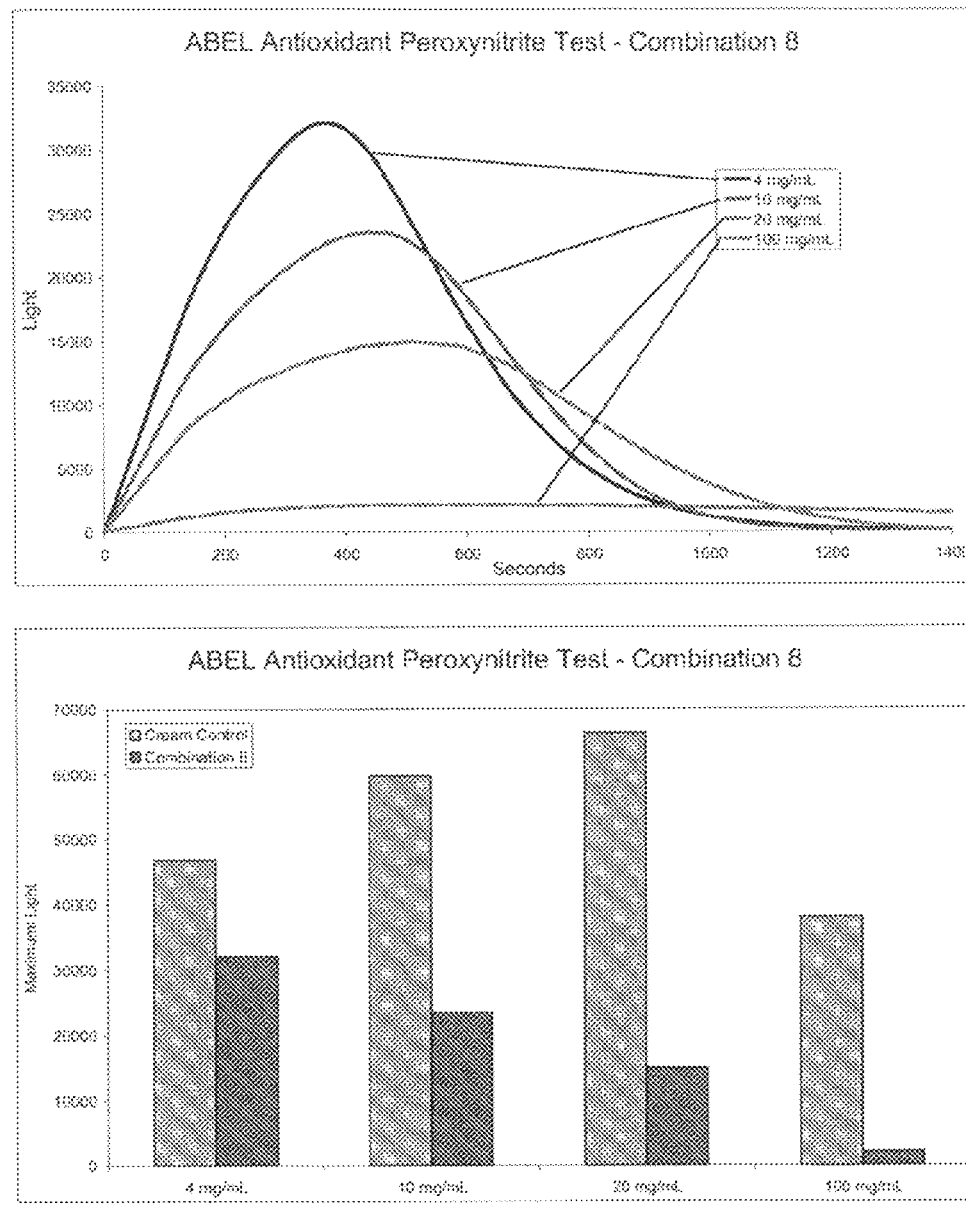

FIGS. 16-18 show the results of the ABEL® antioxidant assay for peroxynitrite, for the base cream containing raw material combinations 1, 8 and 8 modified.

The results of the ABEL® antioxidant assay for peroxynitrite for the cream containing raw material combinations 1, 8 and 8 mod where adjusted to take account of the assay result for the cream control (ie base cream with solvent, but no raw material). The ABEL-RAC scores were then calculated, and are shown in Table 10. The ABEL-RAC scores thus provide measure of the antioxidant effect of the combination of antioxidant agents in the cream—excluding any antioxidant effects shown by the base cream itself.

TABLE 10

ABEL-RAC scores for three cream combinations

| Cream combination number | $EC_{50}$ (mg) | ABEL-RAC |
|---|---|---|
| 1 | 5.0575 | 20 |
| 8 | 3.1703 | 32 |
| 8 modified | 2.2898 | 44 |

The base cream (without solvent or raw material combinations) was also tested, and the results were compared to the results of the cream control (base cream with solvent, no raw material). The result showed that the solvents (water and IMS) only have a minor effect on the peroxynitrite assay.

Example 33

Figure 19:
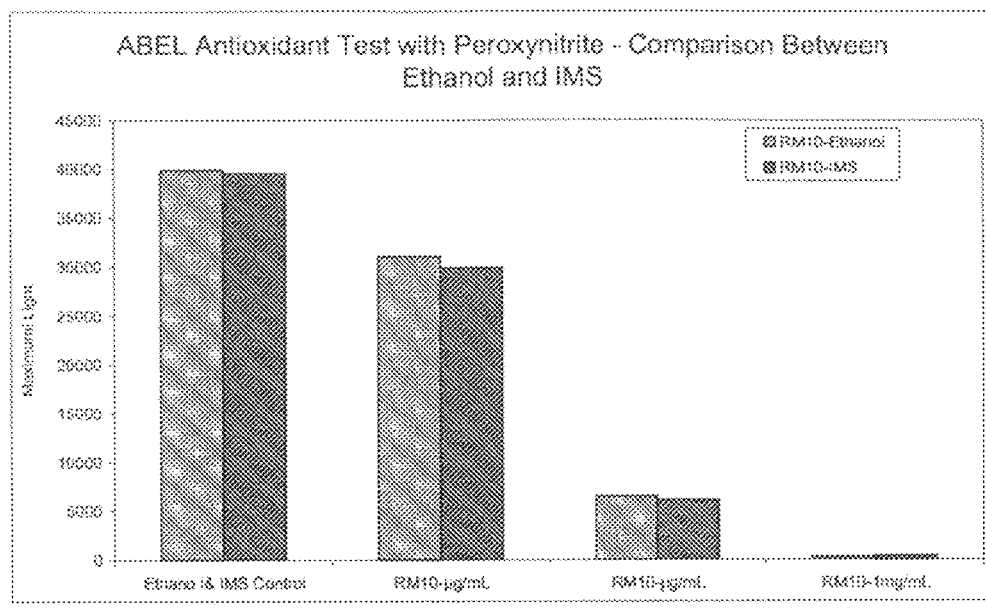
FIG. 19 shows the results of the ABEL® peroxynitrite assay for dimethylmethoxy cromanol diluted with Industrial Methylated Spirits (IMS) and dimethylmethoxy cromanol diluted with ethanol.

Comparison Between the Use of Industrial Methylated Spirits (IMS) and Ethanol as Solvent IMS was the alcohol used as solvent in the initial ABEL® testing. However, ethanol would be used to dilute the relevant raw materials before addition into cosmetic formulations, rather than IMS. The ABEL® peroxynitrite assay for peroxynitrite was run for dimethylmethoxy chromanol diluted with IMS and dimethylmethoxy chromanol diluted with ethanol. The results, shown in FIG. 19, demonstrate that the use of ethanol rather than IMS does not make an appreciable difference. Hence, the results of assays in which ethanol was used as a solvent are considered to be comparable to the results of assays in which IMS was used as a solvent.

Example 34

Antioxidant Testing for a Further Combination of Three Antioxidant Agents from List A Raw material combination 12 comprises raw materials 2, 9 and 10 in the ratio 2:15:2.

The testing method was as described in Example 15, except the relevant raw materials were diluted with ethanol rather than IMS as indicated in Table 11.

TABLE 11

Raw materials and solvents used

| RM name | RM number | Solvent |
|---|---|---|
| ginkgo extract | 2 | 1:1 ethanol:water |
| emblica extract | 9 | water |
| dimethylmethoxy chromanol | 10 | ethanol |

The concentrations of each raw material in cream combination 12 are indicated in Table 12 below.

TABLE 12

Concentration of raw materials used in cream combination 12

| Cream combination number | RM number | Target concentration in cream (%) | Stock concentration of RM in solvent mg/mL |
|---|---|---|---|
| 12 | 2 | 0.02 | 20 |
|  | 9 | 0.015 | 15 |
|  | 10 | 0.02 | 20 |

The cream concentrations that were tested were 1 mg/mL, 5 mg/mL, 10 mg/mL, 25 mg/mL and 50 mg/mL.

The results of the peroxynitrite assay for cream combination 12 are shown in FIG. 20.

The results were adjusted to take account of the assay result for the cream control (ie base cream with solvent, but no raw materials), and the ABEL-RAC score calculated. The score is shown in Table 13, and it indicates the antioxidant effect of the combination of antioxidant agents in the cream (excluding any antioxidant effects shown by the base cream itself).

TABLE 13

ABEL-RAC score for cream combination 12

| Cream combination number | $EC_{50}$ (mg) | ABEL-RAC |
|---|---|---|
| 12 | 2.4268 | 41 |

The invention claimed is:

1. A composition comprising a synergistic combination of ginkgo extract, emblica extract and a further antioxidant agent, wherein said further antioxidant agent is selected from the group consisting of dimethylmethoxy chromanol and rosemary extract and wherein said synergistic combination is in an amount suitable for reducing the risk of or reducing free radical-induced effect on skin and/or hair when topically applied to the skin or hair,
wherein said synergistic combination of ginkgo extract, emblica extract and said further antioxidant agent ranges in amount from 0.0001 to 10% by weight of the total composition, and wherein,
if said further antioxidant agent is dimethylmethoxy chromanol, the ratio by weight of ginkgo extract:emblica extract:dimethylmethoxy chromanol in the composition is ginkgo extract (G): emblica extract (E): dimethylmethoxy chromanol (D), where G is 1, E is 0.5 to 10, and D is 0.05 to 15, and,
if said further antioxidant agent is rosemary extract, the ratio by weight of ginkgo extract:emblica extract:rosemary extract in the composition is 15 to 25:10 to 20:1.

2. The composition of claim 1, comprising ginkgo extract, emblica extract and dimethylmethoxy chromanol in a ratio by weight of 1:0.5 to 10:0.05 to 15.

3. The composition of claim 1, wherein the ratio of G:E:D is about 18:about 13:about 1.8;
about 1.8:about 13:about 18;
about 20:about 15:about 20;
about 5:about 15:about 20; or
about 10:about 15:about 20.

4. A composition as claimed in claim 3, wherein the ratio of G:E:D is about 10:about 15:about 20.

5. The composition of claim 1, further comprising one or more agents selected from the group consisting of white lupin peptides, palmitoyl oligopeptide and palmitoyl tetrapeptides, and retinyl palmitate.

6. The composition of claim 1 further comprising ascorbic acid, or a salt, ester, glucoside, and/or glucosamine derivative thereof.

7. The composition of claim 1, wherein said amount ranges from 0.001% to 1% by weight of the total composition.

8. The composition of claim 7, wherein said amount ranges from 0.001% to 0.1% by weight of the total composition.

9. The composition of claim 1, comprising ginkgo extract, emblica extract and rosemary extract in a ratio by weight of about 18:about 13:1.

10. A method for reducing the risk of or reducing free radical-induced effects on the skin and/or hair in a subject in need thereof, comprising administering an effective amount of the composition of claim 1 to the hair and/or skin of said subject.

11. A composition comprising a synergistic combination of dimethylmethoxy chromanol, pine bark extract and a further antioxidant agent, wherein said further antioxidant is selected from the group consisting of emblica extract and rosemary extract and wherein said synergistic combination is in an amount suitable for reducing the risk of or reducing free radical-induced effect on skin and/or hair when topically applied to the skin or hair,
wherein said synergistic combination of dimethylmethoxy chromanol, pine bark extract and said further antioxidant agent ranges in amount from 0.0001 to 10% by weight of the total composition, and wherein,
if said further antioxidant agent is emblica extract, the ratio by weight of dimethylmethoxy chromanol:pine bark:emblica extract is 0.5 to 3:0.5 to 3:10 to 20, and,
if said further antioxidant agent is rosemary extract, the ratio by weight of dimethylmethoxy chromanol:pine bark:rosemary extract is 15 to 25:15 to 25:10.

12. The composition of claim 11, comprising dimethylmethoxy chromanol, pine bark extract and rosemary extract in a ratio by weight of 15 to 25:15 to 25:10.

13. The composition of claim 11, further comprising one or more agents selected from the group consisting of white lupin peptides, palmitoyl oligopeptide and palmitoyl tetrapeptides, and retinyl palmitate.

14. The composition of claim 11, further comprising ascorbic acid, or a salt, ester, glucoside, glucosamine derivative thereof.

15. The composition of claim 11, wherein said amount ranges from 0.001% to 1% by weight of the total composition.

16. The composition of claim 15, wherein said amount ranges from 0.001% to 0.1% by weight of the total composition.

17. The composition of claim 11, comprising dimethylmethoxy chromanol, pine bark extract and emblica extract in a ratio by weight of about 1.8:about 1.7:about 13.

18. The composition of claim 11, comprising dimethylmethoxy chromanol, pine bark extract and rosemary extract in a ratio by weight of about 18:about 17:about 10.

19. A method for reducing the risk of or reducing free radical-induced effects on the skin and/or hair of a subject in need thereof, comprising administering an effective amount of the composition of claim 11 to the hair and/or skin of the subject in an amount sufficient to reduce the risk of or reduce free radical-induced effects.

* * * * *